United States Patent [19]

Koishikawa et al.

[11] Patent Number: 5,560,247

[45] Date of Patent: Oct. 1, 1996

[54] EXHAUST GAS SAMPLING DEVICE FOR OUTBOARD MOTOR

[75] Inventors: Kouji Koishikawa; Motoyoshi Shishido, both of Wako, Japan

[73] Assignee: Honda Giken Kogyo Kabushiki Kaisha, Tokyo, Japan

[21] Appl. No.: 120,963

[22] Filed: Sep. 15, 1993

[30] Foreign Application Priority Data

| Sep. 16, 1992 | [JP] | Japan | 4-246913 |
| Feb. 5, 1993 | [JP] | Japan | 5-018527 |
| Aug. 31, 1993 | [JP] | Japan | 5-216361 |

[51] Int. Cl.⁶ ................................................. G01N 1/22
[52] U.S. Cl. ................................................. 73/863.81
[58] Field of Search ........................... 73/863.81, 863.85

[56] References Cited

U.S. PATENT DOCUMENTS

| 2,491,418 | 12/1949 | Schlesman | 73/149 |
| 2,666,326 | 1/1957 | Poole et al. | 73/149 |
| 2,785,567 | 3/1957 | Poole et al. | 73/24.05 |
| 2,837,914 | 6/1958 | Caldwell | 73/589 |
| 2,930,237 | 3/1960 | Fowle, Jr. et al. | 73/863.81 X |
| 2,998,723 | 9/1961 | Smith et al. | 73/290 |
| 3,075,382 | 1/1963 | Mathias | 73/149 |
| 3,110,890 | 11/1963 | Westcott et al. | 340/244 |
| 3,163,843 | 12/1964 | Dieckamp | 340/1 |
| 3,237,451 | 3/1966 | Haeff | 73/149 |
| 3,241,368 | 3/1966 | Newitt | 73/290 B |
| 3,252,325 | 5/1966 | Miller | 73/398 |
| 3,286,098 | 11/1966 | Long et al. | 250/230 |
| 3,312,107 | 4/1967 | Burns et al. | 73/149 X |
| 3,324,716 | 6/1967 | Roberts | 73/149 |
| 3,357,245 | 12/1967 | Wolfrum | 73/290 |
| 3,427,652 | 2/1969 | Seay | 166/250 |
| 3,494,185 | 2/1970 | Watanabe et al. | 73/149 |
| 3,540,275 | 11/1970 | Post et al. | 73/290 |
| 3,596,510 | 8/1971 | Paine et al. | 73/149 |
| 3,683,212 | 8/1972 | Zoltan | 310/8.3 |
| 3,693,613 | 9/1972 | Kelman | 128/24 A |
| 3,769,834 | 11/1973 | Fletcher et al. | 73/149 |
| 4,072,046 | 2/1978 | Lao | 73/574 |
| 4,113,434 | 9/1978 | Tancka et al. | 73/863.55 |
| 4,145,881 | 3/1979 | Poullot | 60/276 |
| 4,229,798 | 10/1980 | Rosie et al. | 364/564 |
| 4,303,376 | 12/1981 | Siekmann | 417/360 |
| 4,318,674 | 3/1982 | Godbey et al. | 417/36 |

(List continued on next page.)

FOREIGN PATENT DOCUMENTS

| 0119790 | 9/1984 | European Pat. Off. . | |
| 207946 | 9/1986 | Japan | 73/863.81 |
| 2-51023 | 2/1990 | Japan . | |
| 4-121296 | 4/1992 | Japan . | |
| 4-135998 | 5/1992 | Japan . | |
| 4-166494 | 6/1992 | Japan . | |
| 1558193 | 12/1979 | United Kingdom | 73/863.81 |
| 83/02001 | 6/1983 | WIPO . | |

OTHER PUBLICATIONS

*Patent Abstracts of Japan;* Grp M1317, vol. 16, No. 467 abstract published Sep. 29, 1992 (abstract of Japanese patent No. 4–166494 entitled "Exhaust Device for Outboard Motor").

*Patent Abstracts of Japan* : Grp M1317. vol. 16, No. 467, ABS pub. date Sep. 29, 1992 "Exhaust Device for Outboard Motor"; (abstract of JP 4–166495 published Jun. 12, 1992).

*Primary Examiner*—Thomas P. Noland
*Attorney, Agent, or Firm*—Armstrong, Westerman, Hattori, McLeland & Naughton

[57] ABSTRACT

An exhaust pipe extending from an engine of an outboard motor is covered with an exhaust pipe cover that defines a cooling water passage around an outer periphery of the pipe. An exhaust gas sampling pipe has a base end inserted into the exhaust pipe through the exhaust pipe cover, and a tip end occluded by a detachable plug. The exhaust gas sampling pipe and the plug are accommodated within an engine cover detachably mounted on an upper portion of an undercase, whereby it is protected against rusting due to the deposition of seawater and damaging due to collision against another object.

24 Claims, 27 Drawing Sheets

U.S. PATENT DOCUMENTS

| | | | |
|---|---|---|---|
| 4,341,116 | 7/1982 | Bilstad et al. | 73/290 |
| 4,430,891 | 2/1984 | Holm | 73/149 |
| 4,474,061 | 10/1984 | Parker | 73/149 |
| 4,535,627 | 8/1985 | Prost et al. | 73/290 B |
| 4,561,298 | 12/1985 | Pond | 73/149 |
| 4,599,892 | 7/1986 | Doshi | 73/49.2 |
| 4,640,130 | 2/1987 | Sheng et al. | 73/290 |
| 4,651,555 | 3/1987 | Dam | 73/19 |
| 4,689,553 | 8/1987 | Haddox | 324/58.5 |
| 4,704,902 | 11/1987 | Doshi | 73/149 |
| 4,713,966 | 12/1987 | Thyren et al. | 73/149 |
| 4,754,186 | 6/1988 | Choperena et al. | 310/316 |
| 4,764,166 | 8/1988 | Spani | 604/65 |
| 4,778,451 | 10/1988 | Kamen | 73/149 X |
| 4,808,161 | 2/1989 | Kamen | 73/149 X |
| 4,811,595 | 3/1989 | Marciniak et al. | 73/149 |
| 4,818,186 | 4/1989 | Pastrone et al. | 417/63 |
| 4,821,558 | 4/1989 | Pastrone et al. | 73/19 |
| 4,826,482 | 5/1989 | Kamen | 73/149 X |
| 4,842,584 | 6/1989 | Pastrone et al. | 604/50 |
| 4,874,359 | 10/1989 | White et al. | 604/4 |
| 4,899,573 | 2/1990 | Dimmick et al. | 73/49.2 |
| 4,927,411 | 5/1990 | Pastrone et al. | 604/65 |
| 4,944,191 | 7/1990 | Pastrone et al. | 73/599 |
| 4,949,584 | 8/1990 | Lade et al. | 73/865.8 |
| 4,971,516 | 11/1990 | Lawless et al. | 415/1 |
| 4,976,162 | 12/1990 | Kamen | 364/564 X |
| 4,991,433 | 2/1991 | Warnaka et al. | 73/149 X |
| 5,000,664 | 3/1991 | Lawless et al. | 417/63 |
| 5,211,201 | 5/1993 | Kamen et al. | 604/123 X |
| 5,241,853 | 9/1993 | Tsuei et al. | 73/116 | it is possible to prevent the generation of a rust or corrosion due to deposition of the seawater on an exhaust passage in which the exhaust gas sampling pipe is mounted, thereby avoiding the degradation of the appearance.

EXHAUST GAS SAMPLING DEVICE FOR OUTBOARD MOTOR

BACKGROUND OF THE INVENTION

1. Field of the Invention

The present invention relates to an exhaust gas sampling device for an outboard motor.

2. Description of the Prior Art

In order to analyze noxious components contained in an exhaust gas discharged from an engine of an outboard motor, it is a conventional practice to sample the exhaust gas from an exhaust gas sampling pipe mounted in an exhaust passage and analyze the exhaust gas by a component measuring instrument. There is such a conventionally known exhaust gas sampling device for an outboard motor, which is described in Japanese Patent Application Laid-open No.166495/92.

An exhaust gas sampling pipe in the above prior art exhaust gas sampling device is threadedly inserted into an exhaust pipe and fixed thereto by means of a lock nut, and an opening in the exhaust gas sampling pipe which extends through an outer wall of the outboard motor and which is exposed to the outside, is occluded by a plug. In sampling the exhaust gas, the plug is removed, and the exhaust gas component measuring instrument is connected to the pipe.

In the above prior art exhaust gas sampling device for the outboard motor, however, a tip end of the exhaust gas sampling pipe is exposed to the outside from the outer wall of the outboard motor. Therefore, if the sampling pipe is formed of a material not resistant to rust and corrosion when seawater splashes on the exhaust gas sampling pipe, a rust or corrosion is generated, which causes problems of reduction in durability of the exhaust gas sampling pipe, an inconvenience in the operation of removal of the plug, and a degradation of appearance. The outside plug, further, causes a possibility that the exhaust gas sampling pipe may be damaged by hitching on another object during transportation of the outboard motor or, for example.

SUMMARY OF THE INVENTION

Accordingly, it is a first object of the present invention to improve the durability of the exhaust gas sampling device for the outboard motor.

To achieve the above object, according to the present invention, there is provided an exhaust gas sampling device for an outboard motor comprising an engine, a propeller driven by the engine, case means for rotatably supporting propeller, cover means detachably mounted on the case means, an exhaust passage for introducing an exhaust gas from the engine to a lower portion of the case means, and an exhaust gas sampling pipe connected to the exhaust passage, wherein an opened end of the exhaust gas sampling pipe is disposed within a space which is defined by the case means and the cover means.

With the above construction, by the disposition of the opened end of the exhaust gas sampling pipe in the space defined by the case means and the cover means, it is possible to cover the opened end of the exhaust gas sampling pipe with the case means or the cover means. This avoids the disadvantage that seawater is splashed on the exhaust gas sampling pipe to rust it, even when the pipe is made of a material not so resistant to rust and corrosion or the exhaust gas sampling pipe is hitched on another object during transportation of the outboard motor for example. In addition, it is possible to prevent the generation of a rust or corrosion due to deposition of the seawater on an exhaust passage in which the exhaust gas sampling pipe is mounted, thereby avoiding the degradation of the appearance.

In addition, to achieve the above object, according to the present invention, there is provided an exhaust gas sampling device for an outboard motor comprising an engine, a propeller driven by the engine, case means for rotatably supporting the propeller, an exhaust gas outlet passage which connects an exhaust bore in the engine with an exhaust chamber provided in the case means to introduce an exhaust gas from the engine to a lower portion of the case means, and an exhaust gas sampling pipe which is mounted in an outer wall member defining the exhaust gas outlet passage therein and which is connected to the exhaust gas outlet passage, wherein the exhaust gas sampling pipe is a stud pipe embedded into the outer wall member, and the outer wall member is formed with a sealing surface for a plug occluding the exhaust gas sampling pipe.

With the above construction, by the formation of the exhaust gas sampling pipe from the stud pipe embedded into the outer wall member, it is possible not only to easily fix the exhaust gas sampling pipe, but also to reliably prevent the leakage of the exhaust gas between the outer wall member and the exhaust gas sampling pipe. In addition, by the formation of the sealing surface for the plug for occluding the exhaust gas sampling pipe on the outer wall member, it is possible to prevent the leakage of the exhaust gas and the rusting or corrosion of the exhaust gas sampling pipe due to the deposition of seawater thereon.

Further, to achieve the above object, according to the present invention, there is provided an exhaust gas sampling device of an outboard motor, comprising an engine, a propeller driven by the engine, case means for rotatably supporting the propeller, cover means detachably mounted to the case means, an exhaust gas passage through which an exhaust gas is passed from the engine to a lower portion of the case means, and an exhaust gas sampling pipe connected to the exhaust gas passage, wherein the exhaust gas sampling pipe is formed substantially straight and is mounted to a seat surface formed in an upwardly-directed manner on an outer surface defining a thick wall of the exhaust gas passage. The exhaust gas sampling device further includes a plug located in an internal space defined in the cover means and/or the case means for occluding an opened end of the exhaust gas sampling pipe.

With the above construction, because the plug for occluding the opened end of the exhaust gas sampling pipe is located in the internal space in the cover means and/or the case means, it is possible to avoid rust or corrosion being generated and interfering with the detaching of the plug, when the seawater has splashed on the plug, and to avoid the exhaust gas sampling pipe becoming hitched on another object during transportation of the outboard motor for, example. In addition, because the exhaust gas sampling pipe, formed substantially straight, is mounted to a seat surface formed in an upwardly-directed manner on an outer surface of the thick wall of the exhaust gas passage, it is possible to insure sufficient clearance in the internal space between the opened end of the exhaust gas sampling pipe and the cover means and/or the case means to facilitate the exhaust gas sampling operation. Further, it is possible to prevent the generation of rust or corrosion due to the deposition of the seawater to the exhaust gas passage to which the exhaust gas sampling pipe is mounted, thereby avoiding a degradation of appearance.

The above and other objects, features and advantages of the invention will become apparent from the following description of preferred embodiments, taken in conjunction with the accompanying drawings.

BRIEF DESCRIPTION OF THE DRAWINGS

FIGS. 1 to 6 illustrate a first embodiment of the present invention, wherein

FIG. 1 is a side view of the entire outboard motor;

FIG. 2 is an enlarged sectional view of an essential portion of the outboard motor shown in FIG. 1;

FIG. 3 is a view taken along a line 3—3 in FIG. 2;

FIG. 4 is a view taken along a line 4—4 in FIG. 2;

FIG. 5 is a sectional view taken along a line 5—5 in FIG. 4;

FIG. 6 is a view taken along a line 6—6 in FIG. 2;

FIG. 7 to 11 illustrate a second embodiment of the invention, wherein

FIG. 7 is an enlarged sectional view of an essential portion of an outboard motor according to the second embodiment;

FIG. 8 is a view taken along a line 8—8 in FIG. 7;

FIG. 9 is a view taken along a line 9—9 in FIG. 7;

FIG. 10 is a sectional view taken along a line 10—10 in FIG. 8;

FIG. 11 is an exploded perspective view of an undercover;

FIGS. 19 to 25 illustrate a fourth embodiment of the present invention, wherein

FIG. 19 is a side view of the entire outboard motor;

FIG. 20 is an enlarged sectional view of an essential portion of the outboard motor shown in FIG. 19;

FIG. 21 is a view taken along a line 21—21 in FIG. 20;

FIG. 22 is an enlarged sectional view taken along a line 22—22 in FIG. 20;

FIG. 23 is an enlarged view of the essential portion shown in FIG. 20;

FIG. 24 is an enlarged view taken along a line 24—24 in FIG. 20; and

FIG. 25 is an enlarged view of the essential portion shown in FIG. 20;

FIGS. 26 to 31 illustrate a fifth embodiment of the present invention, wherein

FIG. 26 is a side view of the entire outboard motor;

FIG. 27 is an enlarged view of an essential portion shown in FIG. 26;

FIG. 28 is a sectional view taken along a line 28—28 in FIG. 27;

FIG. 29 is an enlarged sectional view taken along a line 29—29 in FIG. 27;

FIG. 30 is an enlarged sectional view taken along a line 30—30 in FIG. 28; and

FIG. 31 is an enlarged sectional view taken along a line 31—31 in FIG. 28.

DESCRIPTION OF THE PREFERRED EMBODIMENTS

A first embodiment of the present invention will now be described in connection with FIGS. 1 to 6.

Figure 1:
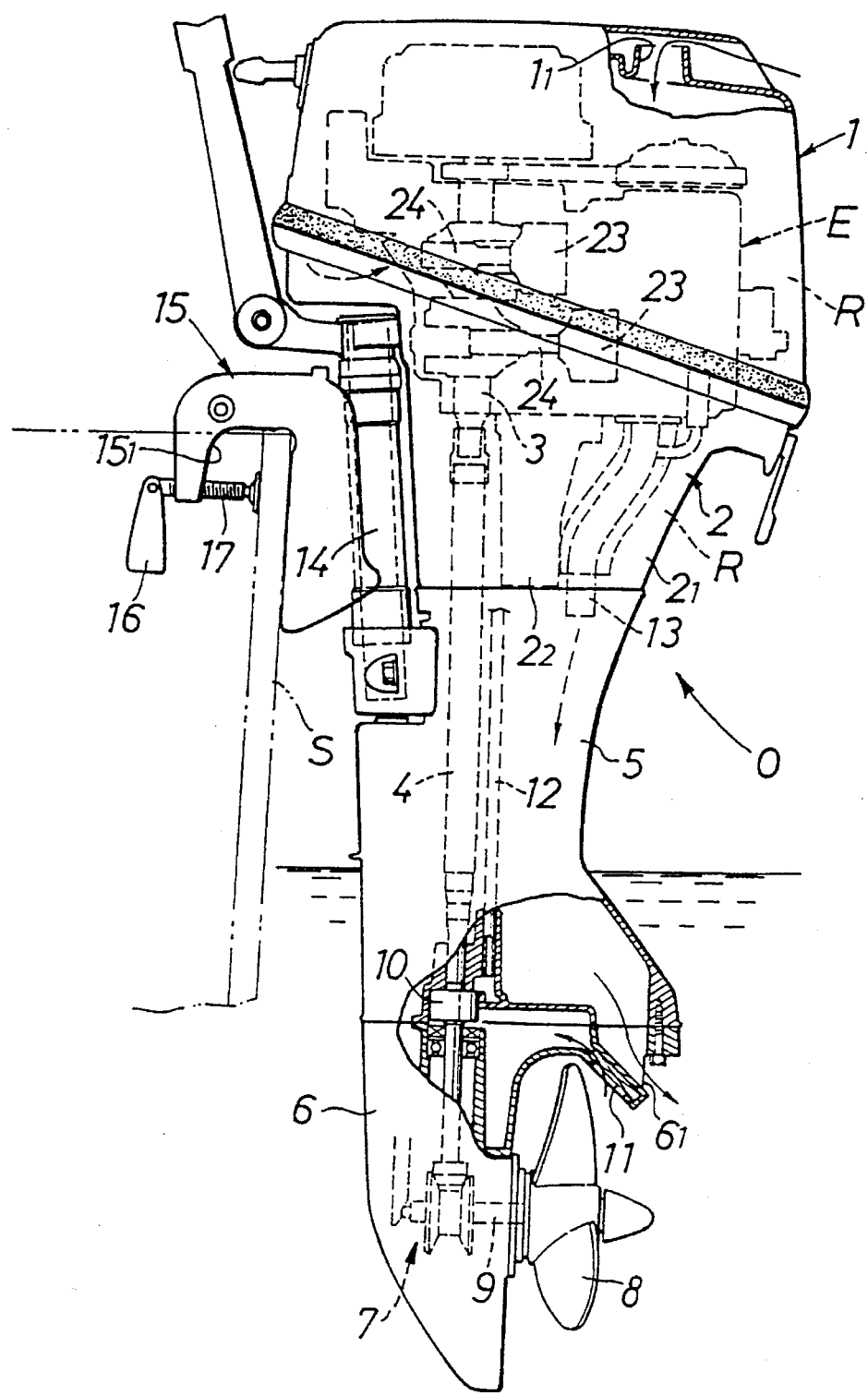

Referring to FIG. 1, a 2-cylinder vertical engine E is mounted in an outboard motor O and covered with an upper cover and a lower case which define an engine room R and which are separable from each other. Specifically, the upper cover is an engine cover 1 for covering an upper half of the engine E, while an oil case 2, integrally provided with a case portion $2_1$ and an oil pan portion $2_2$, for covering a lower half of the engine E. A driving shaft 4 is connected in series to a lower end of a crankshaft 3 of the engine E to extend downwards within an extension case 5 coupled to a lower portion of the oil case 2. A lower end of the driving shaft 4 is connected to a propeller shaft 9 having a propeller 8 at its rear end through a bevel gear mechanism 7 mounted within a gear case 6.

Figure 4:
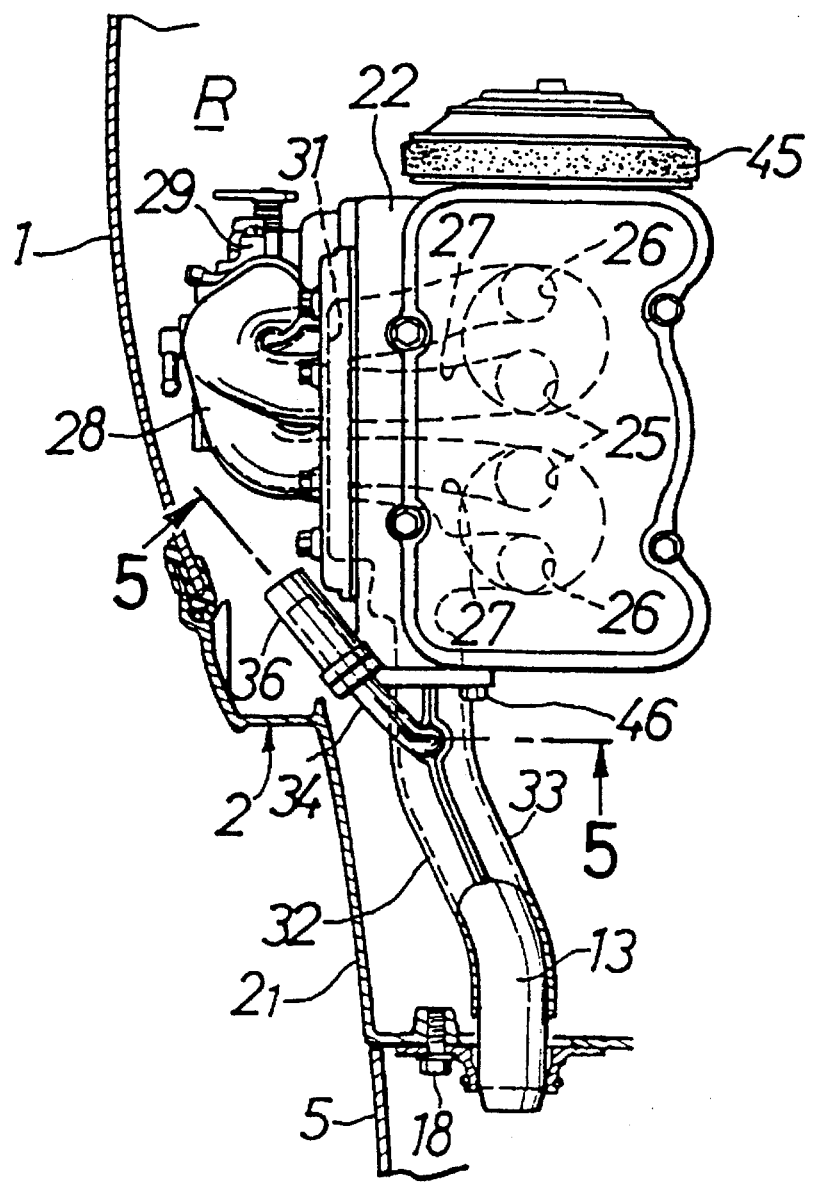

Cooling water is pumped through a filter 11 mounted at a rear portion of the gear case 6, by a cooling-water pump 10, mounted on a lower portion of the driving shaft 4, and is supplied upwards through a cooling-water pipe 12 to cool the engine E. A downward extending discharge pipe 13, FIG. 4, is fixed to the engine E by means of a bolt 46. In coupling the engine E with the discharge pipe 13 mounted thereto to the oil case 2, a lower end of the discharge pipe 13 is fixed to a lower wall of the oil case 2 by means of a bolt 18, FIG. 2, An opening in the lower end of the discharge pipe 13 is opened into the extension case 5. An exhaust gas within the extension case 5 is discharged into the water through an exhaust gas outlet $6_1$, FIG. 1, which is opened into the rear portion of the gear case 6.

A stern bracket 15 for steerably supporting the outboard motor O through a swivel case 14 is fixed by means of a set screw 17 manipulated by a lever 16, and has a groove $15_1$ where a lower end is opened for engagement with a stern S.

Figure 2:
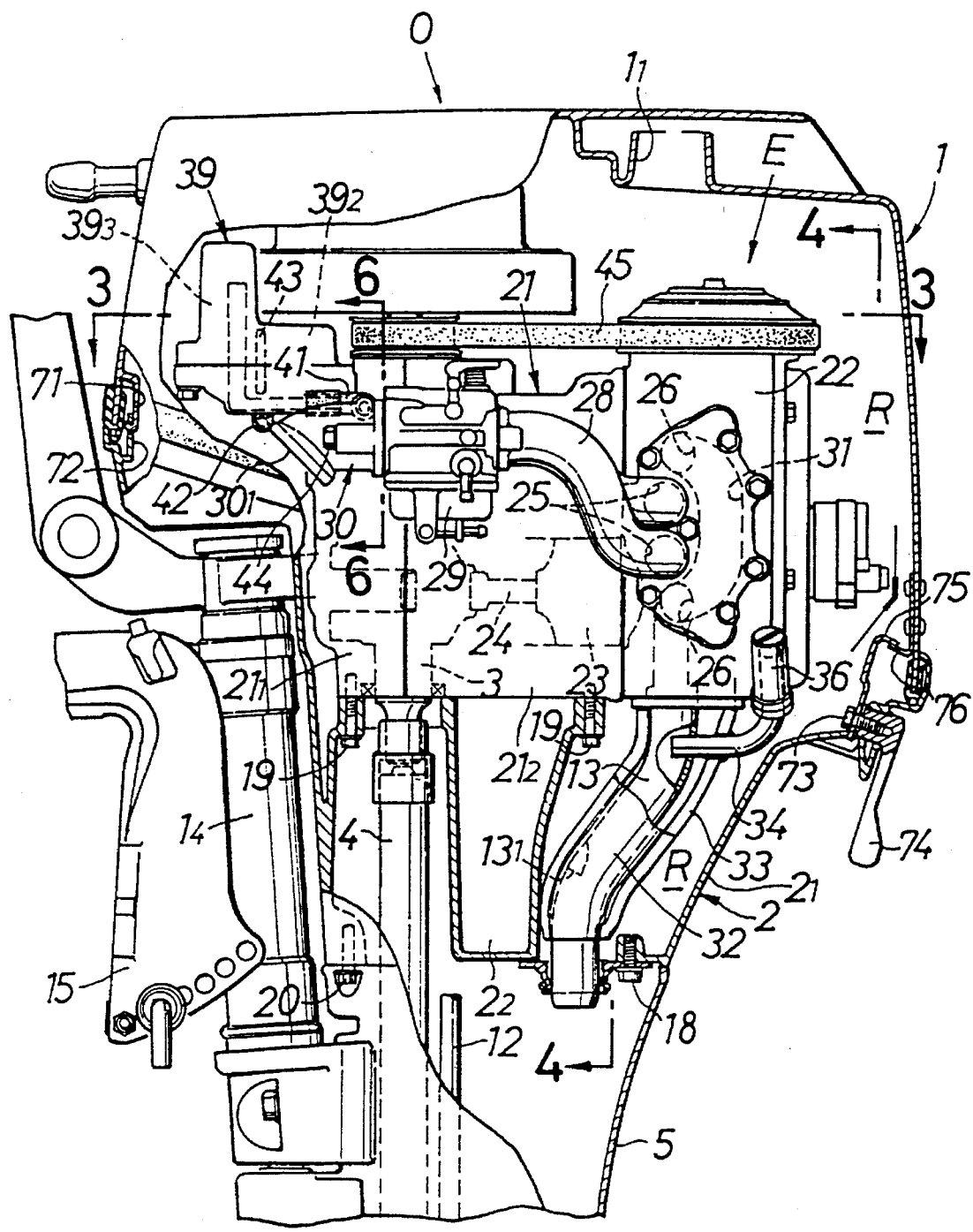
Figure 3:
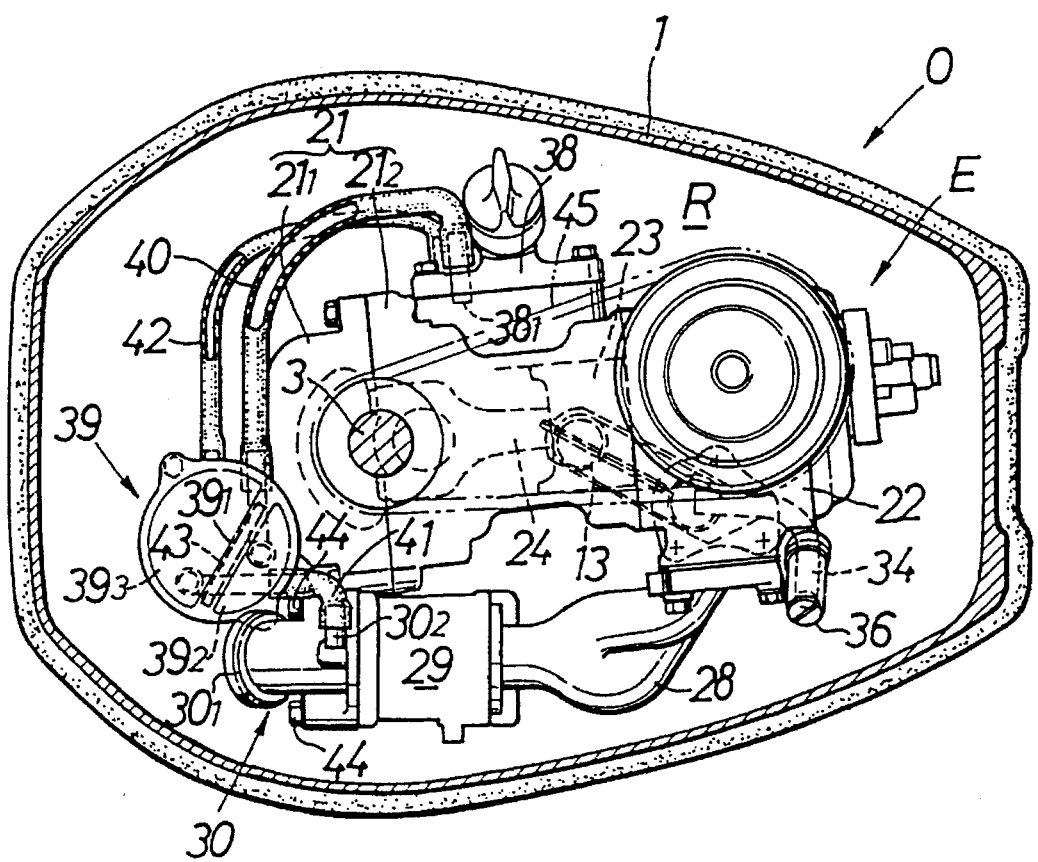

As can be seen from FIGS. 2 to 4, the engine E and the oil case 2 are coupled to each other by means of a plurality of bolts 19, and the extension case 5 and the oil case 2 are coupled to each other by means of a plurality of bolts 20. In addition, the oil case 2 and the engine cover 1 are locked at a front side of the outboard motor O by a hook 71 and a striker 72, and at a rear side of the outboard motor O by a hook lever 74 pivotable about an axis 73, a hook 75 pivotable in unison with the hook lever 74 and a striker member 76.

The engine E of the outboard motor O is longitudinally divided into two parts on a plane including an axis of the crankshaft 3, and includes a cylinder block 21 having a front crankcase $21_1$ defining a portion of a crank chamber and a rear cylinder block portion $21_2$ including a skirt closing the remaining portion of the crank chamber, and a cylinder head 22 coupled to a deck surface of the rear cylinder block portion $21_2$. A pair of pistons 23, 23 are slidably received in the cylinder block 21 and connected to the crankshaft 3 through connecting rods 24, 24, respectively. The cylinder head 22 is provided with a pair of intake bores 25, 25 and a pair of exhaust bores 26, 26. The intake bores 25, 25 communicate with an air inlet $1_1$ opened at an upper portion of the engine cover 1, through two intake ports 27, 27 defined in the cylinder head 22, a bifurcated intake manifold 28, a carburettor 29 having a throttle valve mounted therein, and an air intake 30 opened into the engine cover 1. The exhaust bores 26, 26 communicate with an upper end of the exhaust pipe 13 through a bifurcated exhaust port 31 defined in the cylinder head 22.

Figure 5:
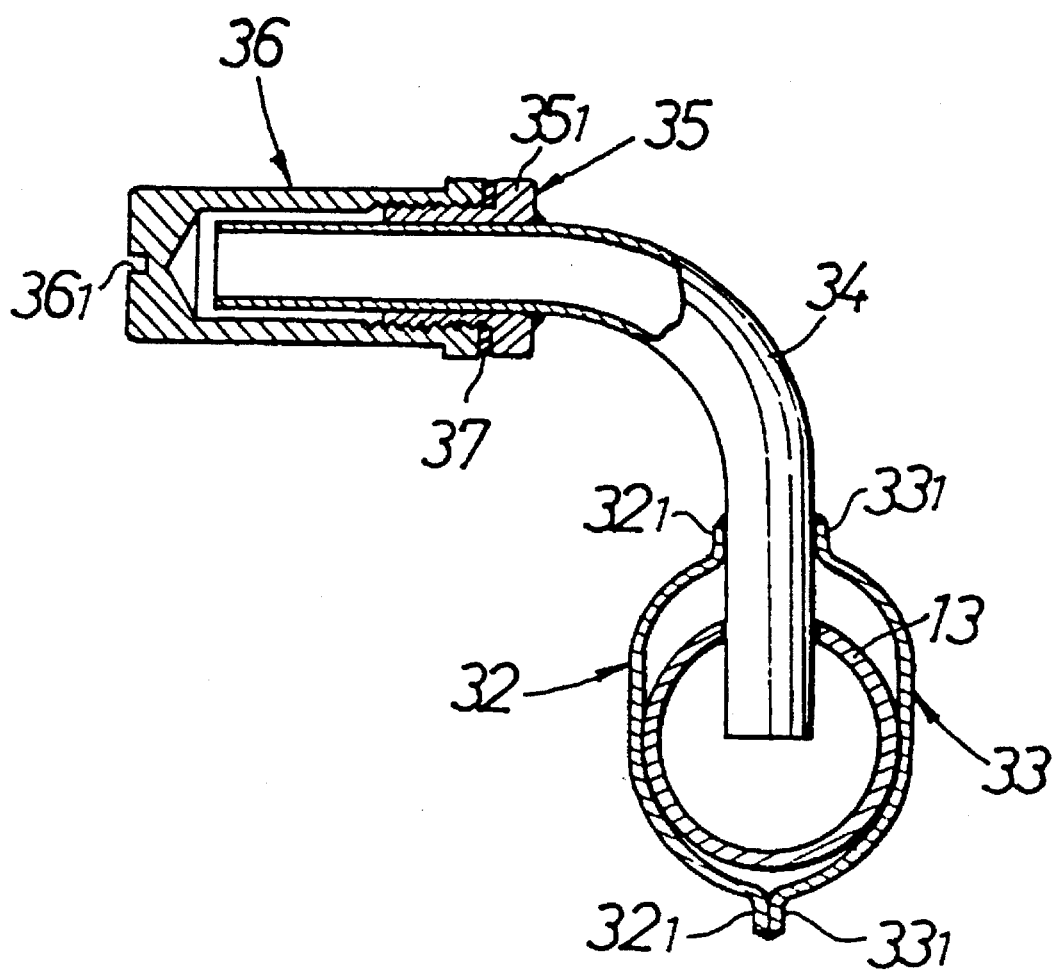

As can be seen from FIGS. 2 to 4 together with FIG. 5, an outer periphery of the exhaust pipe 13 is covered with two-divided exhaust pipe covers 32 and 33, and the cooling water introduced between inner peripheries of the exhaust pipe covers and the outer periphery of the exhaust pipe 13 is permitted to flow through a notch $13_1$ into the exhaust pipe 13 and then flow out of the latter into the extension case 5 together with an exhaust gas. The exhaust pipe covers 32, 33 are integrally welded along their flanges $32_1$ and $33_1$, and an exhaust gas sampling pipe 34 with its tip end inserted into the exhaust pipe 13 is welded around its outer periphery between the flanges $32_1$ and $33_1$, FIG. 5. The exhaust gas sampling pipe 34 extending rearwardly from the exhaust pipe 13 is bent leftwardly at approximately 90°, and extends with its tip end reaching near a junction between the oil case 2 and the engine cover 1. In order to prevent the cooling water from flowing into the exhaust gas sampling pipe 34 to exert an adverse affection to an exhaust gas component measuring instrument, a mounting portion of the exhaust gas sampling pipe 34 is provided above the notch $13_1$ through which the cooling water is introduced into the exhaust pipe 13.

A threaded member 35, FIG. 5, having a flange $35_1$ is welded to the tip end of the exhaust gas sampling pipe 34, and a plug 36 is threadedly fitted over the threaded member 35. Thus, when a tip end of a driver is engaged into a minus groove $36_1$ made in a base end of the plug 36 and then rotated, a sealing member 37 (e.g., washer) is clamped between the tip end of the plug 36 and the flange $35_1$ of the threaded member 35, thereby occluding the tip end of the exhaust gas sampling pipe 34.

In order to inject an oil into the cylinder block 21, an oil filler, FIG. 3, 38 is mounted in an opening defined in a cylinder block wall which communicates with an interior of the crank chamber. The crank chamber is connected with an oil separator 39 mounted in front of the engine E through a small hole 381 provided in the oil filler 38 and through a first blow-by gas passage 40. The separator 39 separates the oil and mist contained in a blow-by gas, and in order to return the separated mist into an intake system, the oil separator 39 and the air intake 30 are connected to each other through a second blow-by gas passage 41.

An interior of the oil separator 39 is partitioned by a partition wall $39_1$, FIG. 3, into a front chamber $39_2$ connected to the first blow-by gas passage 40, and a rear chamber $39_3$ connected to the second blow-by gas passage 41. A bottom of the front chamber $39_2$ is connected with the oil filler 38 through an oil return passage 42, FIGS. 2 and 3, for returning the oil from the oil separator 39 into the cylinder block 21. A one-way valve 43, FIG. 2, is mounted to the partition wall $39_1$ for restraining the back flow of the mist out of the rear chamber $39_3$ into the front chamber $39_2$.

Figure 6:
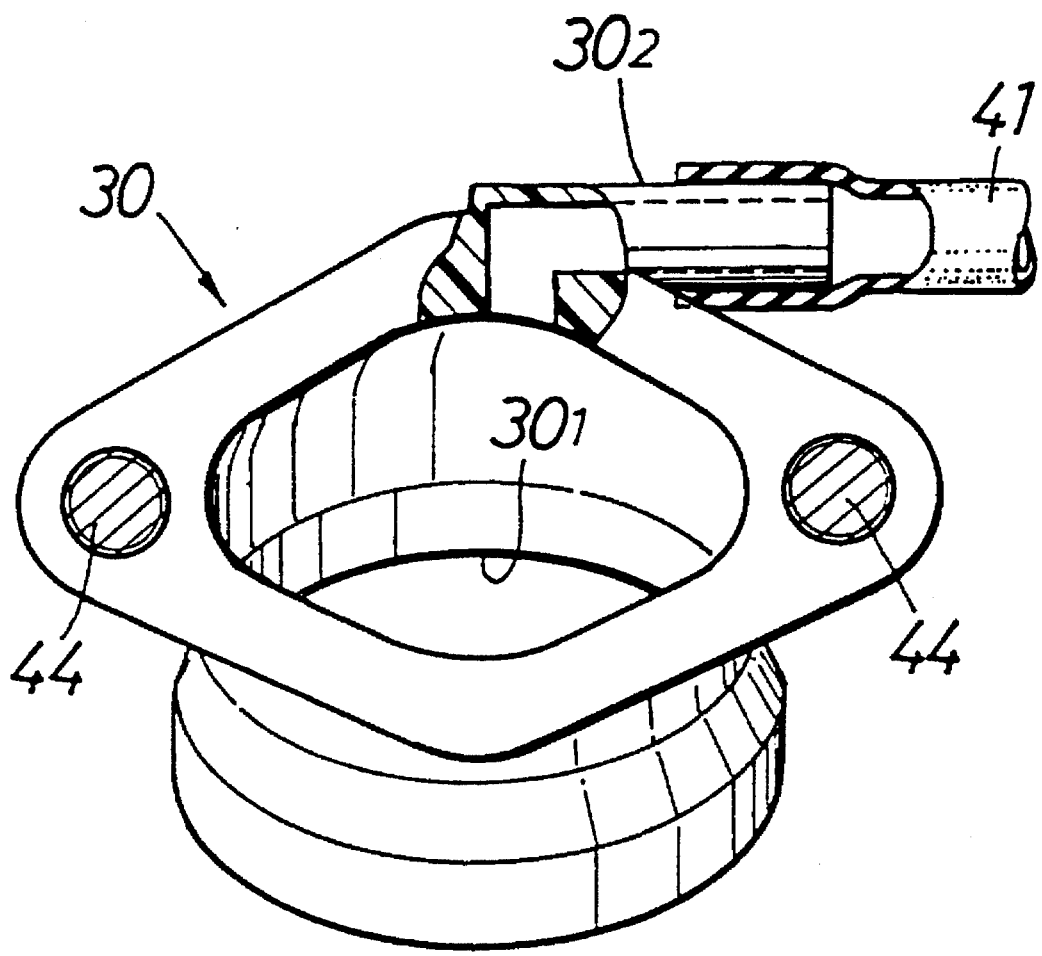

As can be seen from FIGS. 2, 3 and 6, the air intake 30 is fixed with its rear end face mated to a front end face of the carburetor 29 by means of two longitudinally extending bolts 44, 44. An air inlet $30_1$, made in a front end of the air intake 30, is defined so as to be slightly curved downwards, such that water splash entering into the engine cover is prevented from being drawn into the intake system. The air intake 30 has a coupling portion $30_2$ integrally formed on its upper surface to extend toward the engine E perpendicularly to an axis of the air intake 30. The second blow-by gas passage 41 is connected to the coupling portion $30_2$. The coupling portion $30_2$ is disposed at a location offset upwards from axes of the two bolts 44, 44 fixing the air intake 30. Therefore, the attaching and detaching operations for the bolts 44, 44 and the second blow-by gas passage 41 can be performed without any problems. Moreover, because the coupling portion $30_2$ extends toward the engine E, i.e., away from the engine cover 1, there is no probability that the second blow-by gas passage 41 may be damaged, when the engine cover 1 is attached or detached.

It is noted here that reference character 45 in FIG. 2 designates an endless belt for transmitting the rotation of the crankshaft 3 to a valve-operating mechanism.

The operation of the first embodiment of the present invention having the above-described construction will be described below.

An open air drawn through the air inlet 11 into the engine cover 1 is drawn through the air intake 30 into the carburetor 29, where it is mixed with a fuel. Then, the air-fuel mixture is supplied through the intake ports 27, 27 defined in the cylinder head 22 into combustion chambers. An exhaust gas generated in the combustion chambers is introduced through the exhaust port 31 defined in the cylinder head 22 into the exhaust pipe 13, and is passed out of the latter through the inside of the extension case 5 and then discharged through the exhaust gas outlet $6_1$ into the water. During this time, the cooling water pumped by the cooling-water pump 10 mounted on the driving shaft 4 is passed through the inside of a water jacket (which is not shown) in the engine E, and a portion of such cooling water is supplied into between the exhaust pipe 13 and the exhaust pipe covers 32 and 33 to cool the exhaust pipe 13. The cooling water which has cooled the exhaust pipe 13 flows through the notch $13_1$ into the exhaust pipe 13 and is then discharged into the extension case 5 together with the exhaust gas.

A blow-by gas, leaked out of the combustion chamber of the engine E into the cylinder block 21, is supplied through the first blow-by gas passage 40 into the oil separator 39. The mist resulting from the separation of the oil in the oil separator 39 is returned through the second blow-by gas passage 41 into the air intake 30 and is then supplied into the carburettor 29 together with the air flowing in the air intake 30. The oil separated in the separator 39 is returned through the oil return passage 42 and the oil filler 38 into the cylinder block 21.

Now, to examine the components in the exhaust gas from the engine E, the engine cover 1 is loosened and removed from the oil case 2, following which the plug 36, threadedly fitted over the tip end of the exhaust gas sampling pipe 34 may be removed, and the exhaust gas component measuring instrument may be connected thereto.

When the measurement is to be carried out, the engine cover 1 is attached again to the oil case 2, but a piping, such as a tube connected to the component measuring instrument and, at the other end to sampling pipe 34, is led through the air inlet 11 in the engine cover 1 or an opening in the oil case 2 occluded by a grommet or the like, to the outside of the outboard motor O.

Because the exhaust gas sampling pipe 34 is supported on the exhaust pipe 13, integral with the engine E and moreover, the tip end of the exhaust gas sampling pipe 34 is opened into the engine cover 1 and the oil case 2 without penetrating them, it is possible to easily perform the assembling of the engine E including the exhaust gas sampling pipe 34. Further, the plug 36 for occluding the tip end of the exhaust gas sampling pipe 34 is covered with the engine cover 1 and the oil case 2, such that it is shielded from seawater. Therefore, it is possible not only to avoid a salt being deposited to the minus groove $36_1$ in the plug 36, thereby making it difficult for a tip end of a driver to engage the minus groove, and causing a rust or corrosion to be generated on the plug 36, so that the minus groove $36_1$ is destroyed when the driver is rotated, but also to make the plug 36 inconspicuous to provide an improved appearance.

FIGS. 7 to 11 illustrate a second embodiment of the present invention.

Figure 7:
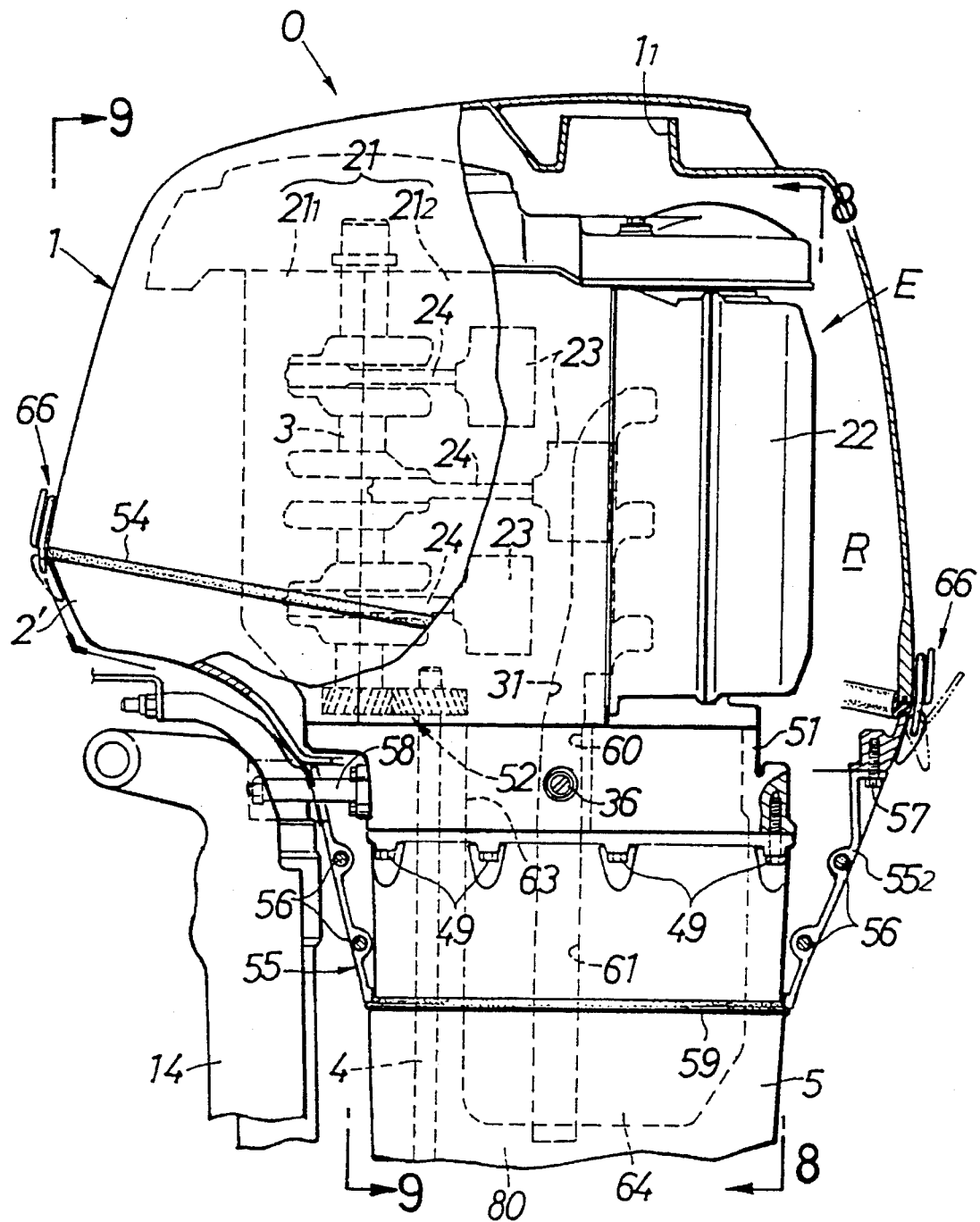

As shown in FIG. 7, an outboard motor O includes a mounting member 51 for supporting a primary gear case or an engine E to the extension case 5. The mounting member 51 is placed on an upper portion of the extension case 5 and coupled thereto by means of a plurality of bolts 49, and a 3-cylinder vertical engine E is coupled to an upper portion of the mounting member 51 by means of plurality of a bolts 50, FIG. 8. A primary reduction mechanism 52, FIG. 7, comprising a pair of helical gears is interposed between a lower end of the crankshaft 3 of the engine E and an upper end of the driving shaft 4.

Figure 8:
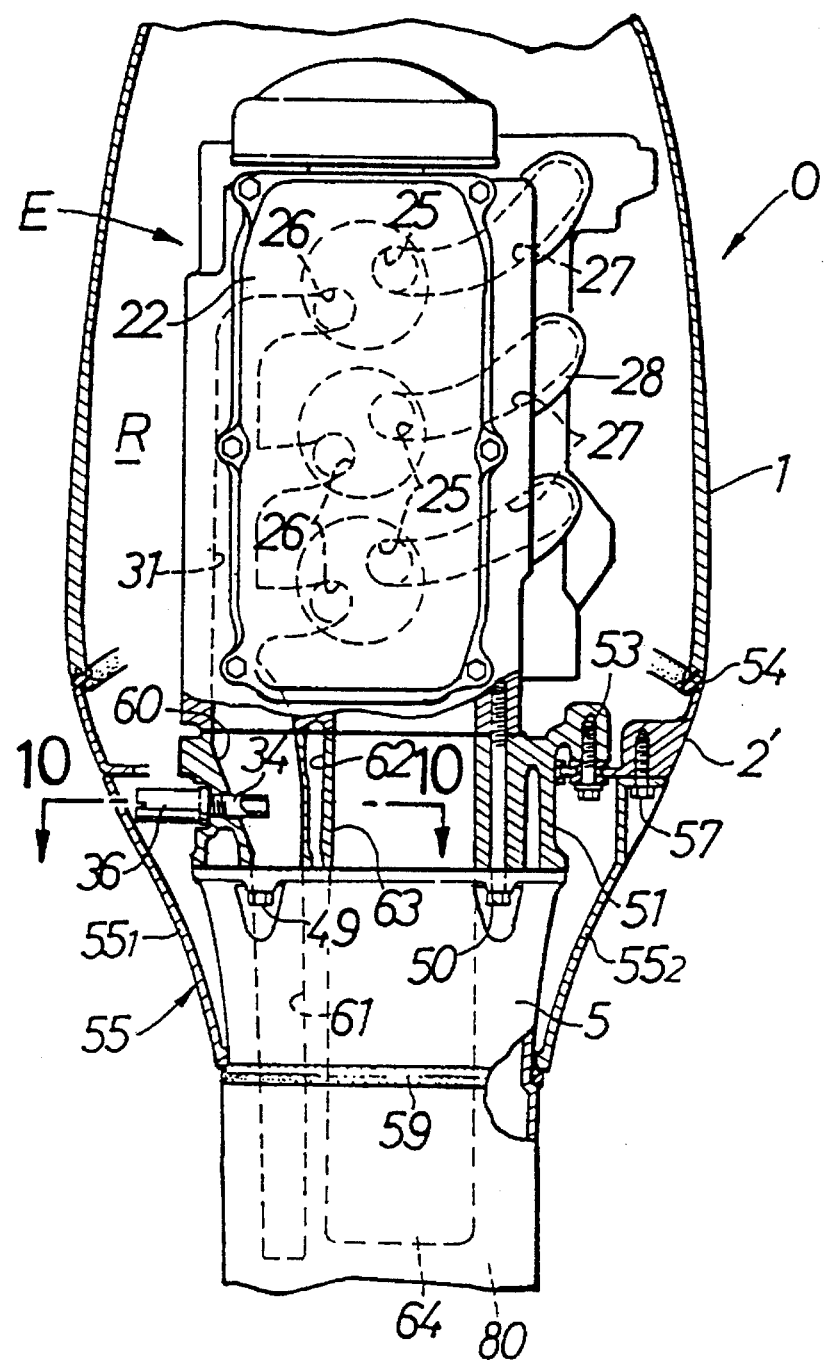
Figure 9:
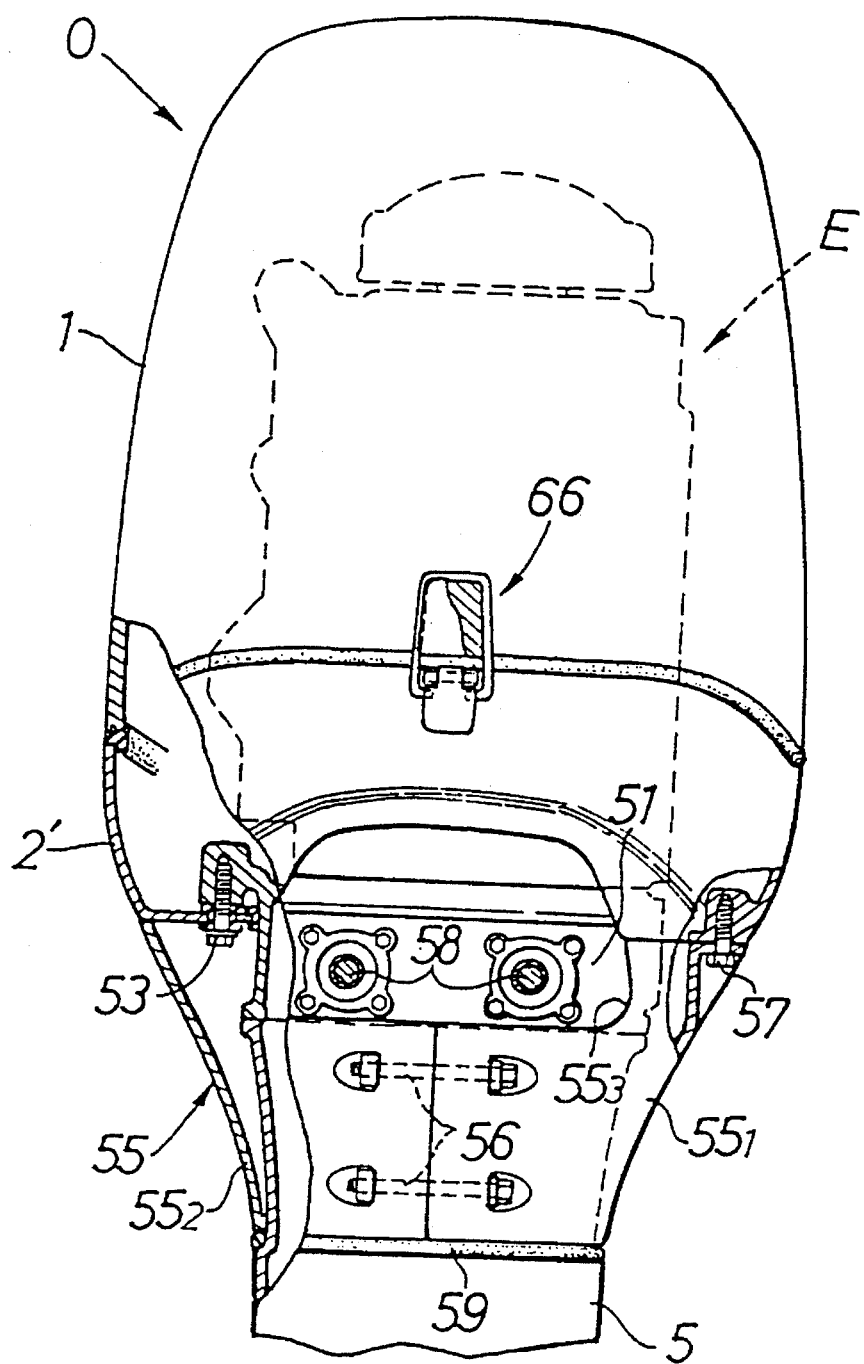
Figure 11:
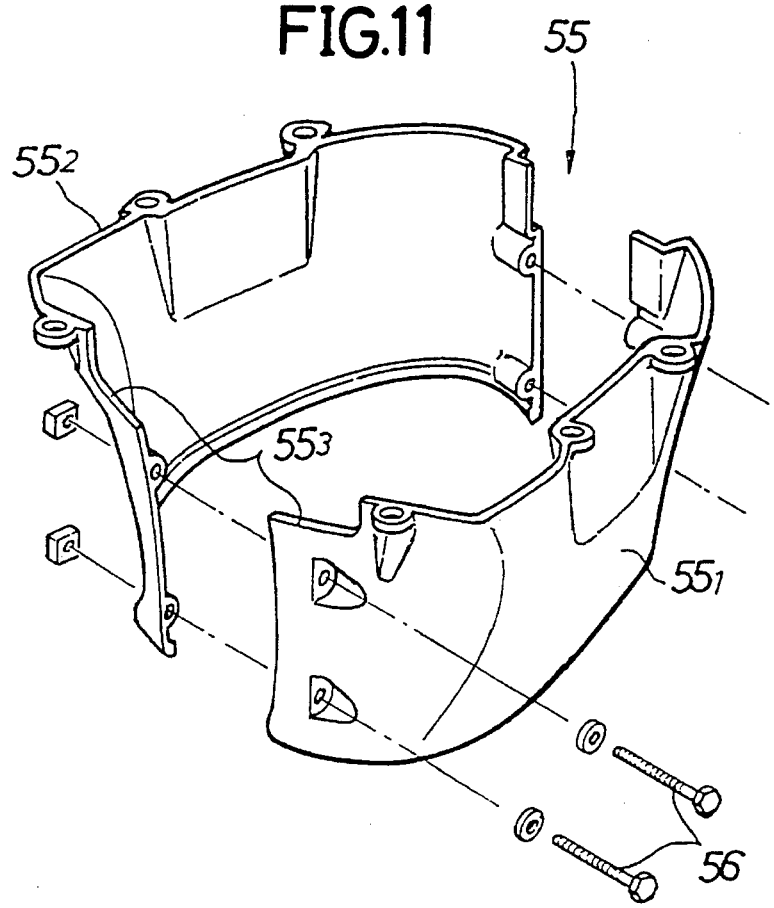

As can be seen from the combination of FIGS. 8, 9 and 11, an undercase 2' opened at its upper end is secured to the mounting member 51 by means of a plurality of bolts 53, and an engine cover 1 is detachably supported on an upper portion of the undercase 2' with a sealing member interposed therebetween. The undercase 2' and the engine cover 1 are releasably coupled to each other by a pair of front and rear buckle-type grips 66, 66, FIG. 7. An undercover 55, detachably mounted on a lower portion of the undercase 2' is divided into two parts and comprises a left cover half $55_1$ and a right cover half $55_2$ which are integrally coupled to each other by means of a plurality of bolts 56. The cover halves $55_1$ and $55_2$ are releasably supported on a lower surface of the undercase 2' by means of a plurality of bolts 57.

A U-shaped notch $55_3$ opened at its upper end is defined in a front surface of the undercover 55. A pair of left and right upper mounts 58, 58 are provided on a front surface of the mounting member 51 for supporting the swivel case 14 and extend forwardly through the notch $55_3$ in the undercover 55. A lower end of the undercover 55 is fitted to a step formed at the vertically middle portion of the extension case 5 with a sealing member 59 interposed therebetween.

The exhaust port 31 defined in the rear crankcase $21_2$ communicates with an exhaust passage 60 defined in the mounting member 51, and further, the exhaust passage 60 communicates with an exhaust pipe 61 which is opened into an exhaust chamber 80 defined in the extension case 5. A water jacket 62 is defined around the exhaust passage 60 in the mounting member 51 and communicates with a water jacket (not shown) defined in the rear crankcase $21_2$. An oil passage 63 is defined in the mounting member 51 in parallel to the exhaust passage 60, and the engine E and an oil pan 64 communicates with each other through the oil passage 63.

Figure 10:
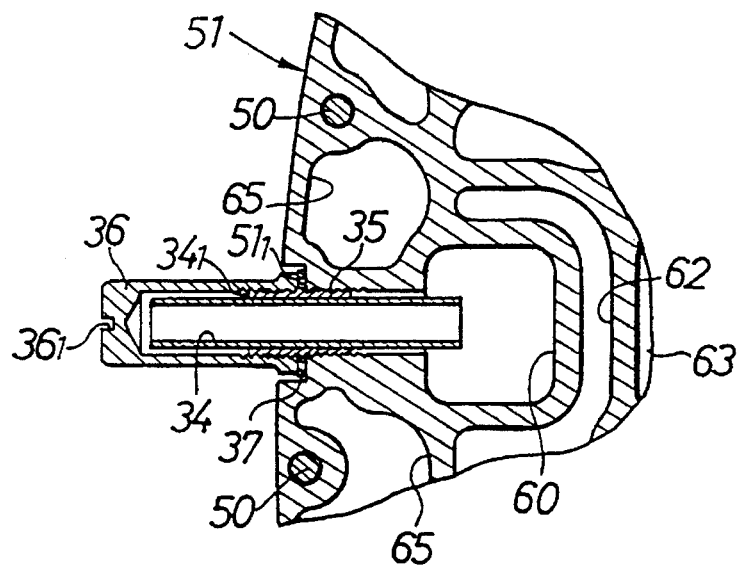

As best shown in FIG. 10, the exhaust gas sampling pipe 34 is comprised of a stud pipe with a threaded member 35 integrally welded around an outer periphery thereof. The exhaust gas sampling pipe 34 is threadedly fitted into a left side of the mounting member 51 through the threaded member 35, and has a base end opened into an exhaust gas outlet passage (the exhaust passage 60 in the illustrated embodiment) including the exhaust port 31 and the exhaust passage 60. A tip end of the exhaust gas sampling pipe 34 extends to near a central portion of a space between the mounting member 51 and the undercover 55. The threaded member 35 has an abutment $34_1$ formed at an outer end thereof, against which a jig for threadedly fitting the exhaust gas sampling pipe 34 into the mounting member 51 abuts.

The exhaust gas sampling pipe 34 is constructed by the stud pipe as described above. Therefore, the need for a lock nut for fixing the exhaust gas sampling pipe 34 is eliminated, leading to a decreased number of parts, and an improved sealability is provided between the exhaust gas sampling pipe 34 and the mounting member 51, thereby reliably preventing the leakage of the exhaust gas and moreover, it is possible to easily position the opening of the exhaust gas sampling pipe 34 within the exhaust gas outlet passage. In addition, the formation of the abutment $34_1$ for the jig on the exhaust gas sampling pipe 34 ensures that as compared with the formation of a hexagonal jig receiving portion (e.g., a nut portion) on the exhaust gas sampling pipe 34, the outside diameter of the exhaust gas sampling pipe 34 can be reduced to diminish a wasteful portion to be cut by machining, and moreover, it is possible to easily mount the exhaust gas sampling pipe 34 to a narrow portion.

The tip end of the exhaust gas sampling pipe 34 is occluded by the same plug 36 and sealing member 37 (e.g., washer) as in the first embodiment. In this case, a sealing surface $51_1$ against which the opening in the plug 36 abuts through the sealing member 37 is formed by utilizing an outer surface of the mounting member 51. Because the sealing surface $51_1$ is formed by utilizing the outer surface of the mounting member 51 in this manner, the sealing can be performed reliably and easily by the plug 36, thereby not only preventing the leakage of the exhaust gas through the plug 36, but also previously avoiding a disadvantageous growth of rust or corrosion due to the deposition of seawater on the exhaust gas sampling pipe 34. It is noted here that reference character 65 in FIG. 10 designates a wall-perforated bore.

To sample the exhaust gas from the engine E, the bolts 56 and 57 may be loosened to remove the undercover 55 from the undercase 2°, following which the plug 36 may be removed from the exhaust gas sampling pipe 34, and the exhaust gas component measuring instrument may be connected thereto. When the outboard motor O is in a normal service state, the tip of the exhaust gas sampling pipe 34 is covered with the undercover 55 and hence, there is no fear that salts may be deposited on the exhaust gas sampling pipe 34 to rust it and that the exhaust gas sampling pipe 34 may be hitched on another object during transportation thereof. It should be noted that because the undercover 55 is divided into the two parts in the embodiment, only one of them may be removed, leading to an excellent workability.

Figure 12:
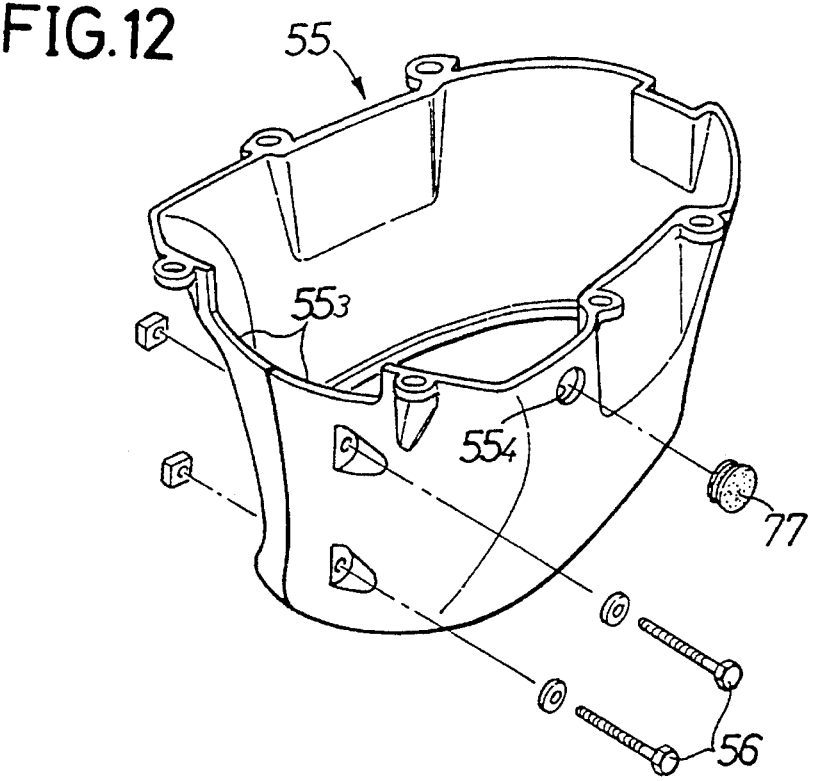
FIGS. 12 and 13 illustrate a modification to the undercover, FIG. 12 being a view similar to FIG. 11, and FIG. 13 being a sectional view of an undercover illustrating a section in the vicinity of an exhaust gas sampling pipe.
Figure 13:
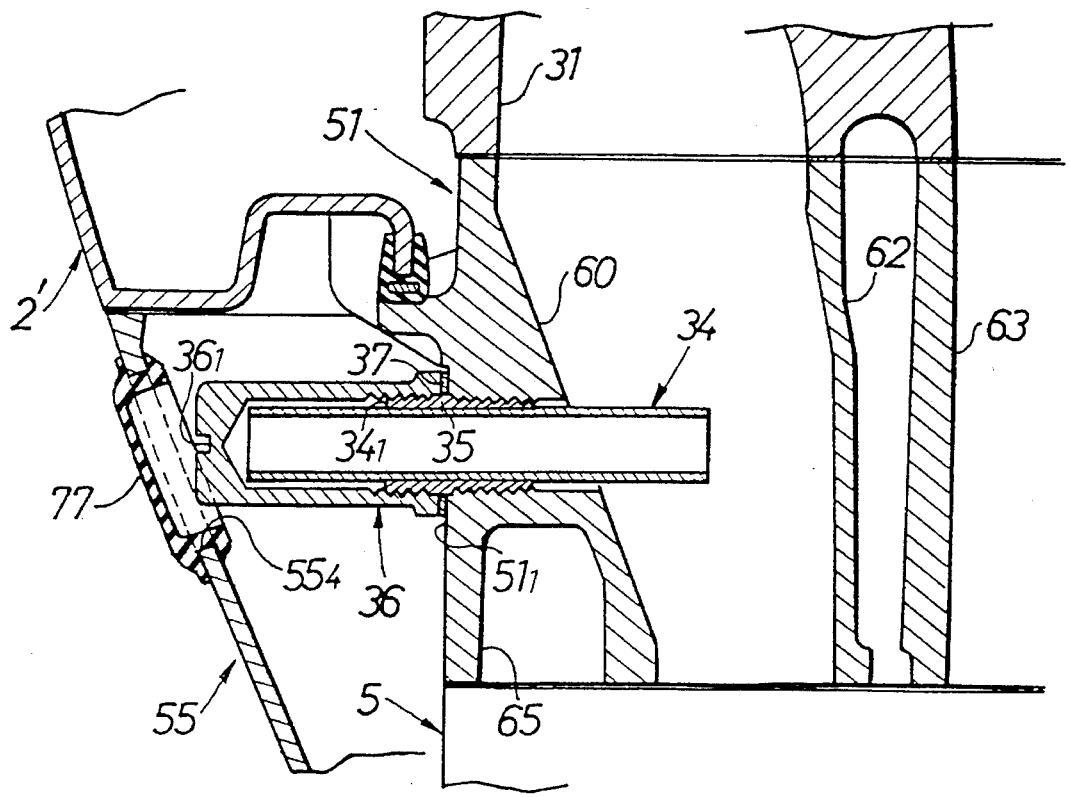

FIGS. 12 and 13 illustrate a modification to the undercover 55 in the second embodiment.

In this modification, an undercover 55 includes a left cover half $55_1$ and a right cover half $55_2$ which are however, integrally formed with each other continuously at their rear portion. A circular opening $55_4$ is made by boring, or the like, at a location on the undercover 55 to which an exhaust gas sampling pipe 34 faces. When the measurement is not carried out, this opening $55_4$ is occluded by a rubber cap 77.

Figure 14:
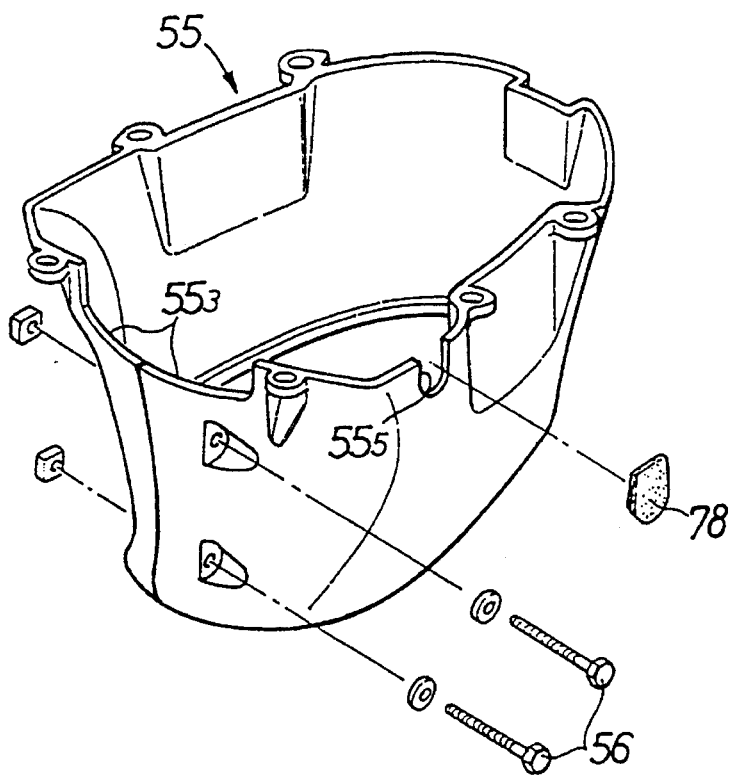
FIGS. 14 and 15 illustrate another modification to the undercover, FIG. 14 being a view similar to FIG. 11, and FIG. 15 being a sectional view of an undercover illustrating a section in the vicinity of the exhaust gas sampling pipe.
Figure 15:
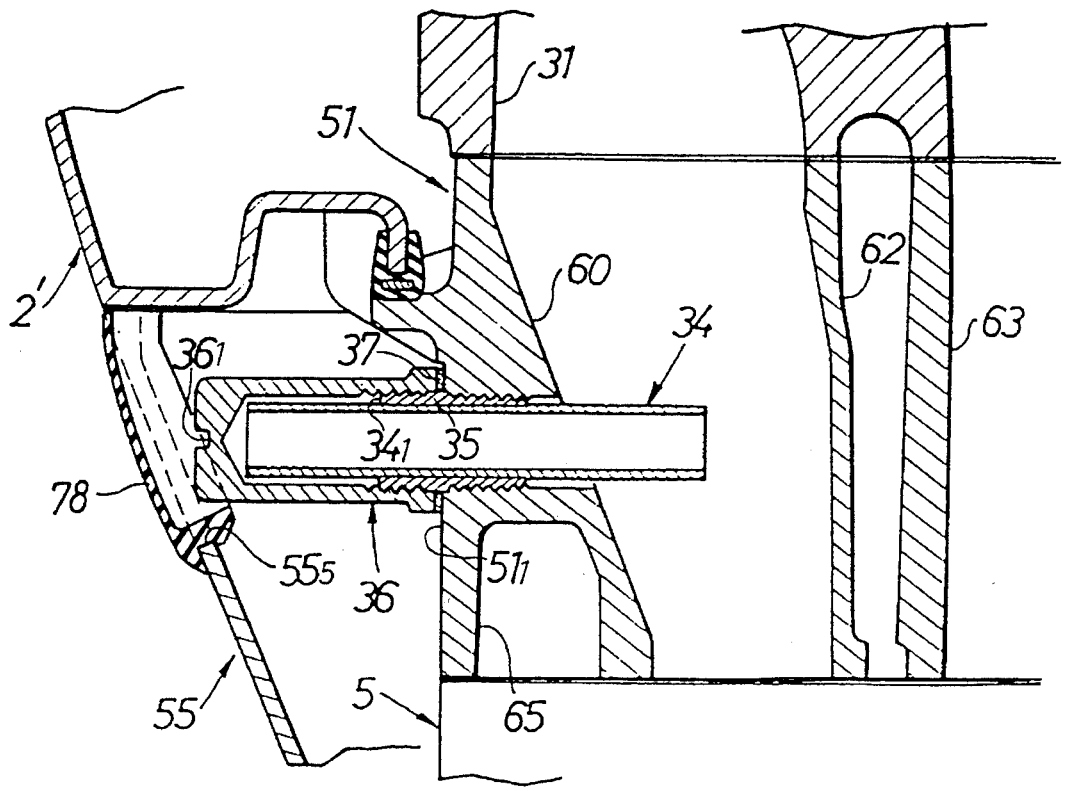

FIGS. 14 and 15 illustrate another modification to the undercover 55 in the second embodiment.

In this modification, a U-shaped opening $55_5$ is made simultaneously upon stamping from the above, at a location on an integrally formed undercover 55 to which an exhaust gas sampling pipe 34 faces. When the measurement is the carried out, the opening $55_5$ is occluded by a rubber cap 78 having an edge confronting to an upper edge of the undercover 55.

According to the modifications shown in FIGS. 12 to 15, it is possible to measure the components of the exhaust gas without removal of the engine cover 1 and the undercover 55, leading to a substantially improved workability.

Figure 16:
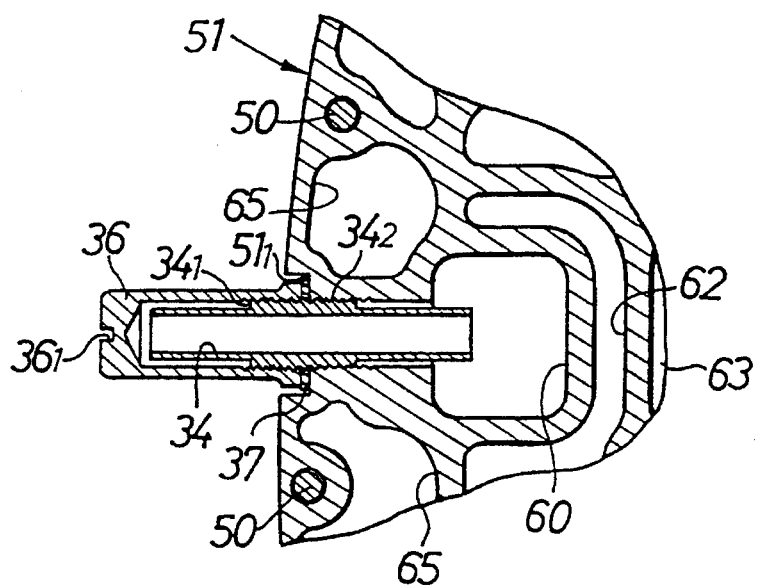
FIGS. 16 and 17 illustrate a modification to the exhaust gas sampling pipe, FIG. 16 being a view similar to FIG. 10, and FIG. 17 being a view similar to FIG. 13.
Figure 17:
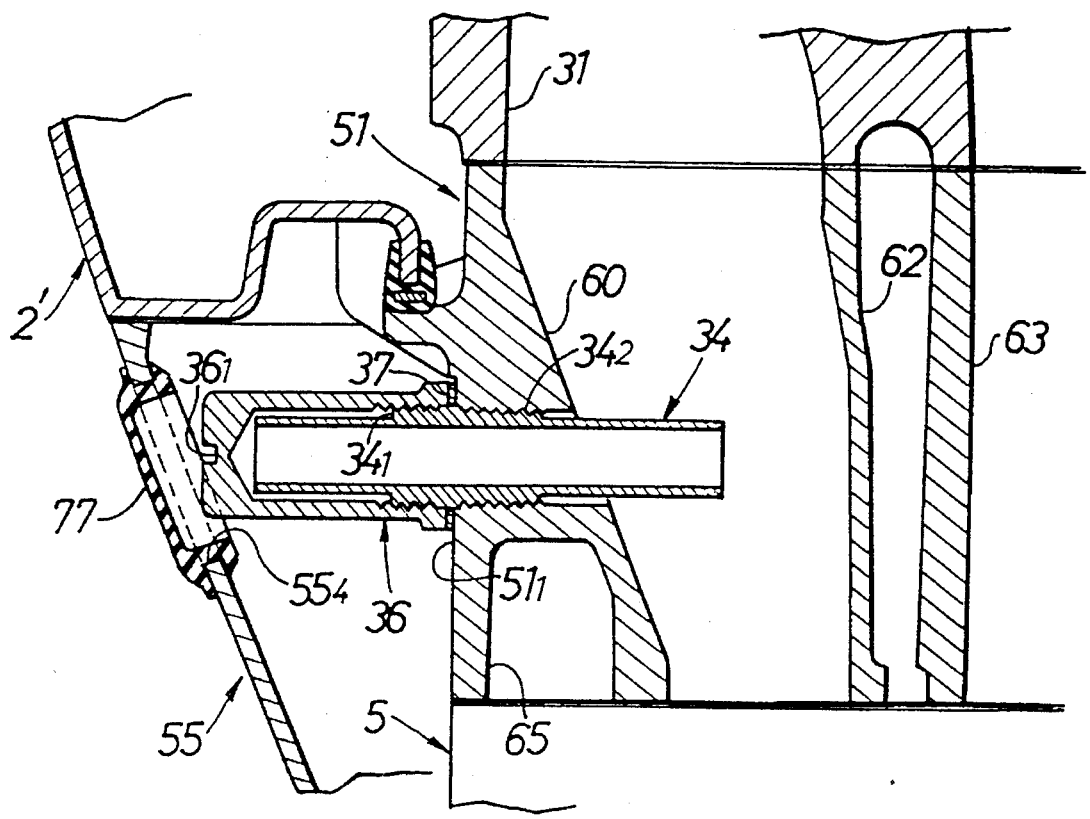

FIGS. 16 and 17 illustrate a modification to the exhaust gas sampling pipe 34 of the second embodiment.

An exhaust gas sampling pipe 34 of this modification has a threaded portion $34_2$ integrally formed thereon, in place of the threaded member 35 secured by welding around the outer periphery of the exhaust gas sampling pipe 34 of the second embodiment. The threaded portion $34_2$ has an abutment $34_1$ integrally formed at its end, to which a jig abuts. According to this modification, it is possible to further reduce the number of parts.

Figure 18:
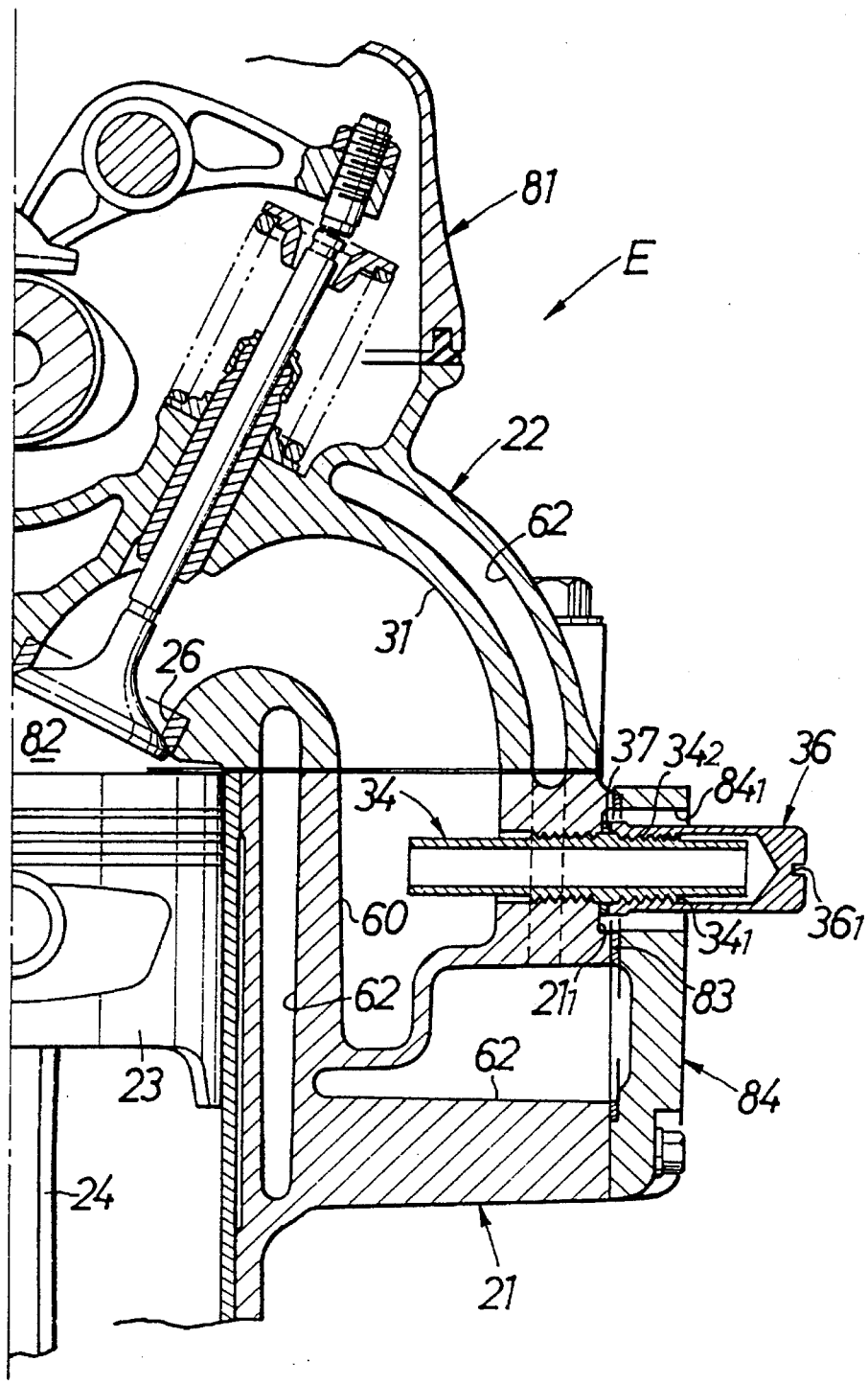
FIG. 18 is an enlarged sectional view of an essential portion of an outboard motor according to a third embodiment of the present invention.

FIG. 18 illustrates a third embodiment of the present invention.

This embodiment has a feature in a mounting position for an exhaust gas sampling pipe 34. More specifically, although the exhaust gas sampling pipe 34 in the second embodiment is threadedly fitted into the mounting member 51 clamped between the cylinder block 21 and the extension case 5, the exhaust gas sampling pipe 34 in this third embodiment is threadedly fitted into the cylinder block 21.

This will be described in further detail. The cylinder head 22 and a head cover 81 are overlaid on the deck surface of the cylinder block 21 of the engine E. And an exhaust opening 26 is formed in a combustion chamber 82 defined in the cylinder head 22 and communicates with the exhaust port 31 defined in the cylinder head 22 and with the exhaust passage 60 defined in the cylinder block 21. The exhaust port 31 and exhaust passage 60 constitute an exhaust outlet passage, as in the first embodiment. The periphery of the exhaust outlet passage is surrounded by a water jacket 62, a portion of which is defined by a cover 84 coupled to an outer wall of the cylinder block 21 with a sealing member 83 interposed therebetween.

An exhaust gas sampling pipe 34 having the same structure as the exhaust gas sampling pipe 34 shown in FIGS. 16 and 17 is threadedly fitted into the outer wall of the cylinder head 21. The exhaust gas sampling pipe 34 is threadedly fitted into the cylinder head 21 through an opening $84_1$ in the cover 84. A base end of the pipe 34 is opened into a lower portion of the exhaust outlet passage (i.e., into the exhaust passage 60 defined in the cylinder head 21), and a tip end of the pipe 34 is occluded by a plug 36 having the same structure as the plug 36 shown in FIGS. 16 and 17. The tip end of the pipe 34 is contained in an engine room. A sealing surface 21, on which the plug 36 is seated with a sealing member 37 interposed therebetween, is formed on an outer surface of the cylinder block 21.

Even with the third embodiment, it is possible to provide an operational effect similar to that in the second embodiment.

A fourth embodiment of the present invention will now be described with reference to FIGS. 19 to 25.

Figure 19:
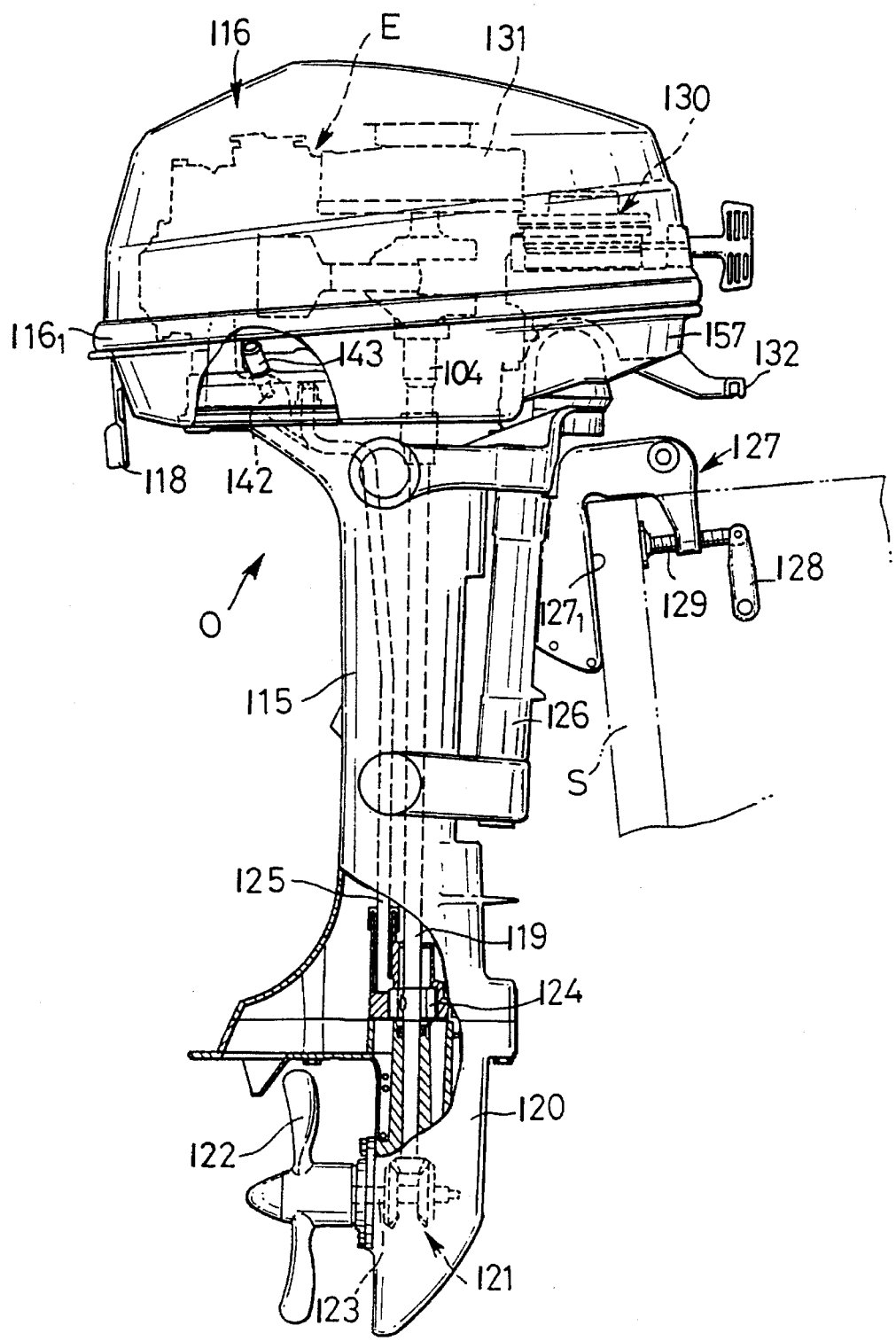
Figure 20:
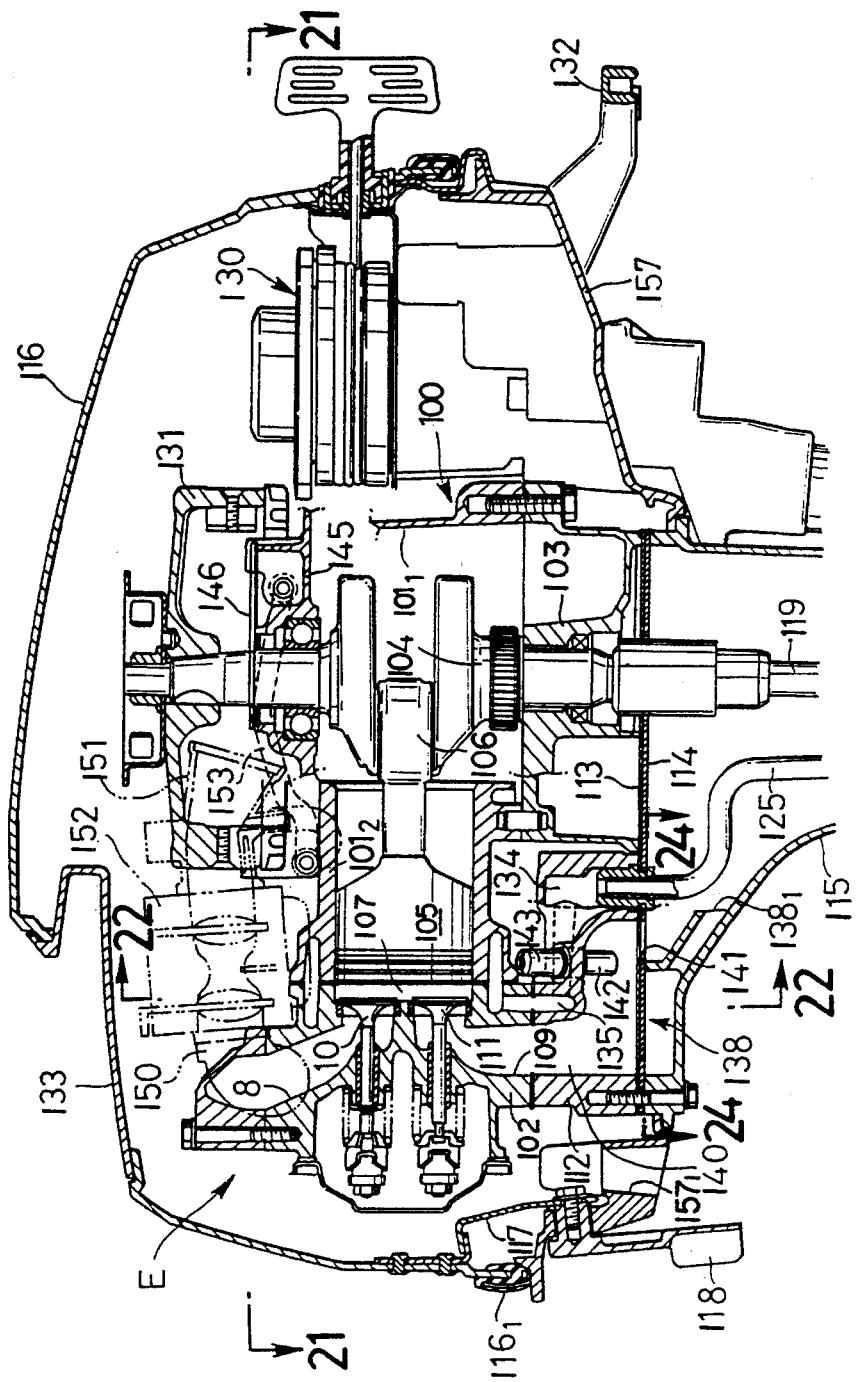

As shown in FIG. 19 and 20, a single-cylinder type vertical engine E mounted in an upper portion of an outboard engine O includes an engine block 101 integrally provided with a crank case portion $10_1$, and a cylinder block $101_2$, and a cylinder head 2 coupled to the cylinder block portion $101_2$ of the engine block 101. A vertically disposed crankshaft 104 is rotatably supported at its opposite ends on an upper wall of the crank case portion $101_1$ of the engine block 101 and on an oil pan 103 coupled to a lower portion of the crank case portion $101_1$. A piston 105 is slidably received in the cylinder block portion $101_2$ of the engine block 1 and connected to the crankshaft 104 through a connecting rod 106. An intake port 108 and an exhaust port 109 are defined in the cylinder head 102 and connected to a combustion chamber 107. The intake port 108 and the exhaust port 109 are opened and closed by an intake valve 110 and an exhaust valve 111 which are connected to a valve operating mechanism which is not shown.

A lower surface of an exhaust block 112 coupled to a lower surface of the cylinder head 102, and a lower surface of the oil pan 103 are coupled to an upper surface of an extension case 115 through a gasket 113 and a partition plate 114 (see FIGS. 22 and 23), whereby the engine E is supported on an upper portion of the extension case 115. An undercase 157 is fixed to a peripheral edge of the upper surface of the extension case 115 by a bolt which is not shown. The undercase 157 has an opening its upper surface, which is covered with an engine cover 116 of synthetic resin. The undercase 57 and the engine cover 116 are separatably coupled to each other by a bracket 117 extending downwardly from the engine cover 116 and by a lever 118 for screwing the bracket 17. A sealing member $161_1$ is mounted around an outer periphery of the engine cover 116 forming a sealing junction with the undercase 157.

A drive shaft 119 is connected in series to a lower end of the crankshaft 104 of the engine E and extends downwardly within the extension case 115. A lower end of the drive shaft 119 is connected to a propeller shaft 123 having a propeller 122 at its rear end through a bevel gear mechanism 121 mounted within a gear case 120. Thus, cooling water is pumped by a cooling water pump 124 provided at a lower portion of the drive shaft 119, and is supplied through a cooling water pipe 125 to the engine E.

A stern bracket 127 for steerably supporting the outboard motor O through a swivel case 126 is fixed by a set screw 129 operated by a lever 128 in a condition in which a groove $127_1$ opened at its lower end is in engagement with a stern S.

Figure 21:
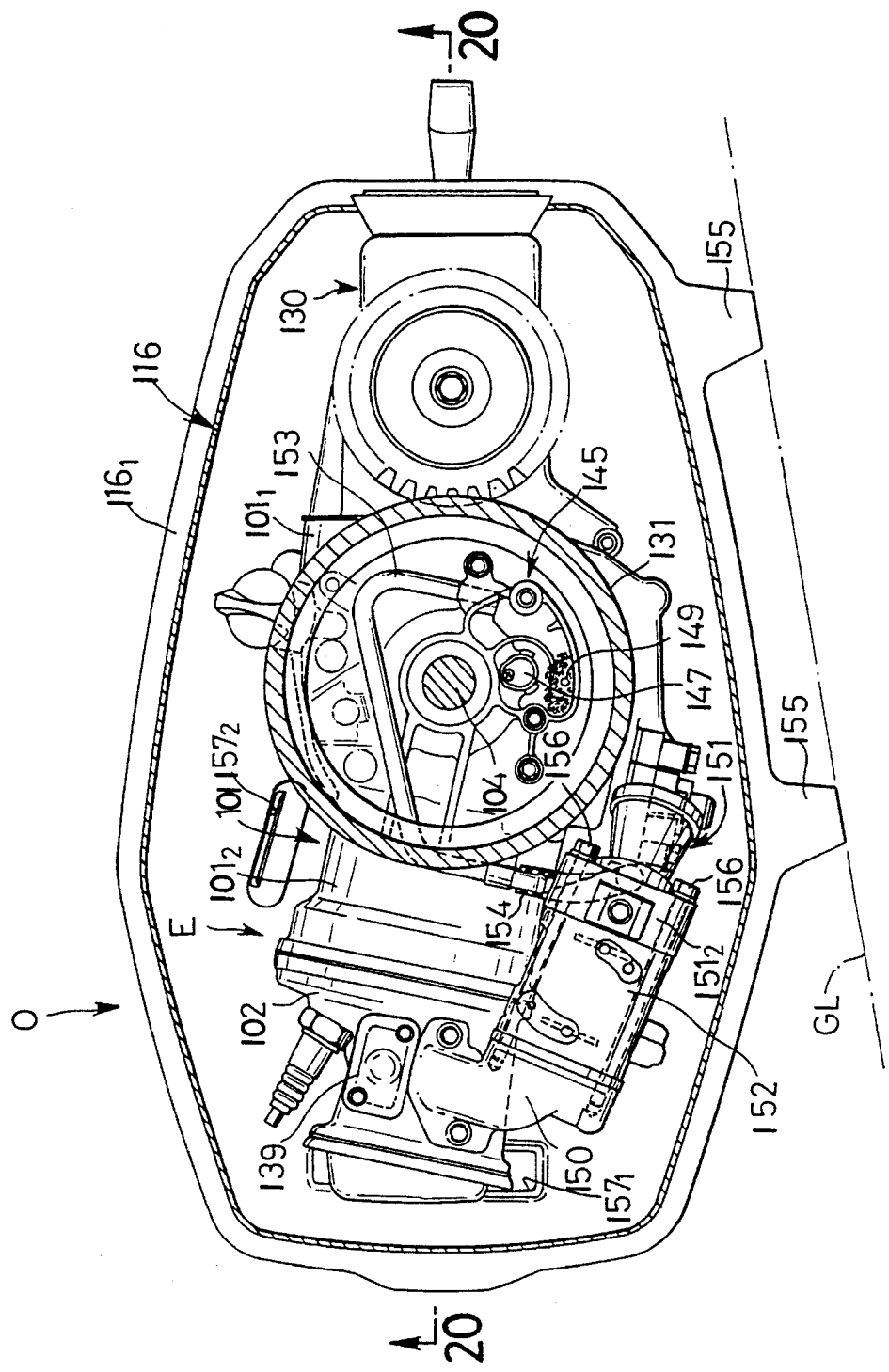

In FIG. 20, reference character 130 is a recoil starter; reference character 131 is a flywheel mounted at an upper end of the crankshaft 104; reference character 132 is a carrying handle for transporting the outboard motor O; and reference character 133 is a lid for closing a maintenance opening defined in the engine cover 116. Reference characters $157_1$ and $157_2$ in FIG. 21 are each an air inlet provided in the undercase 57 for introducing the open air into an engine room. The outboard motor O is steered by a steering handle which is not shown.

As can be seen from FIGS. 20 to 24, an upper end of the cooling water pipe 125 extending upwardly from the cooling water pump 124 is connected to a lower end of a cooling water passage 134 of an L-shape as viewed from the side, which is defined in the exhaust block 112. An upper end of the cooling water passage 134 in the exhaust block 112 is connected to a water jacket 135 formed in the cylinder head 102 and the cylinder block section $101_2$ so as to surround an outer periphery of the combustion chamber 107. The upper end of the water jacket 135 is connected to a cooling water passage 136 defined outside of the water jacket 135. The cooling water passage 136 extends downwardly within the cylinder head 2 and the exhaust block 112 and communicates with a cooling water passage 138 defined between the partition plate 114 and the extension case 115 through an opening 137 defined in the gasket 113 and the partition plate 114. The cooling water passage 138 is opened into the extension case 115 through a drainage hole $138_1$.

Thus, the cooling water pumped by the cooling water pump 24 is discharged from the cooling water pipe 125 through the cooling water passage 134 in the exhaust block 12, the water jacket 135 in the cylinder head 102 and the cylinder block portion $101_2$, the cooling water passage 136 in the cylinder head 102 and the exhaust block 112, the opening 137, the cooling water passage 138 in the extension case 115 and the drainage hole 138, into the extension case 115, while cooling the cylinder head 102, the cylinder block portion $101_2$ and the exhaust block 12. It should be noted that during warming-up of the engine E, a thermostat 139 (see FIG. 22) mounted at an upper end of the water jacket 135 is closed to inhibit the flow of the cooling water, thereby promoting the warming-up of the engine E.

An exhaust passage 140 is defined in the exhaust block 112 and connected to the exhaust port 109 in the cylinder head 102. The exhaust passage 140 communicates with an interior of the extension case 115 through an opening 141, FIG. 20, defined in the gasket 113 and the partition plate 114.

Figure 22:
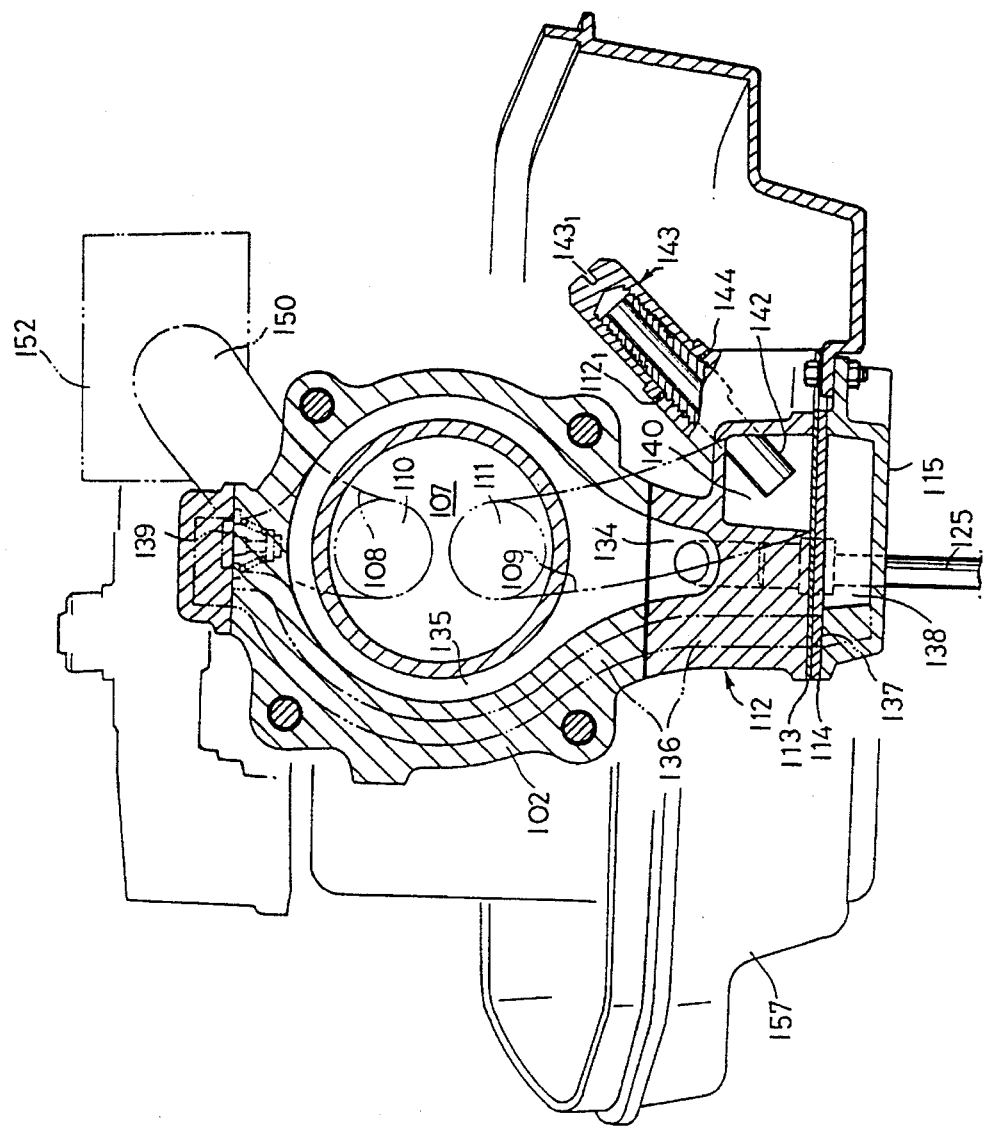
Figure 23:
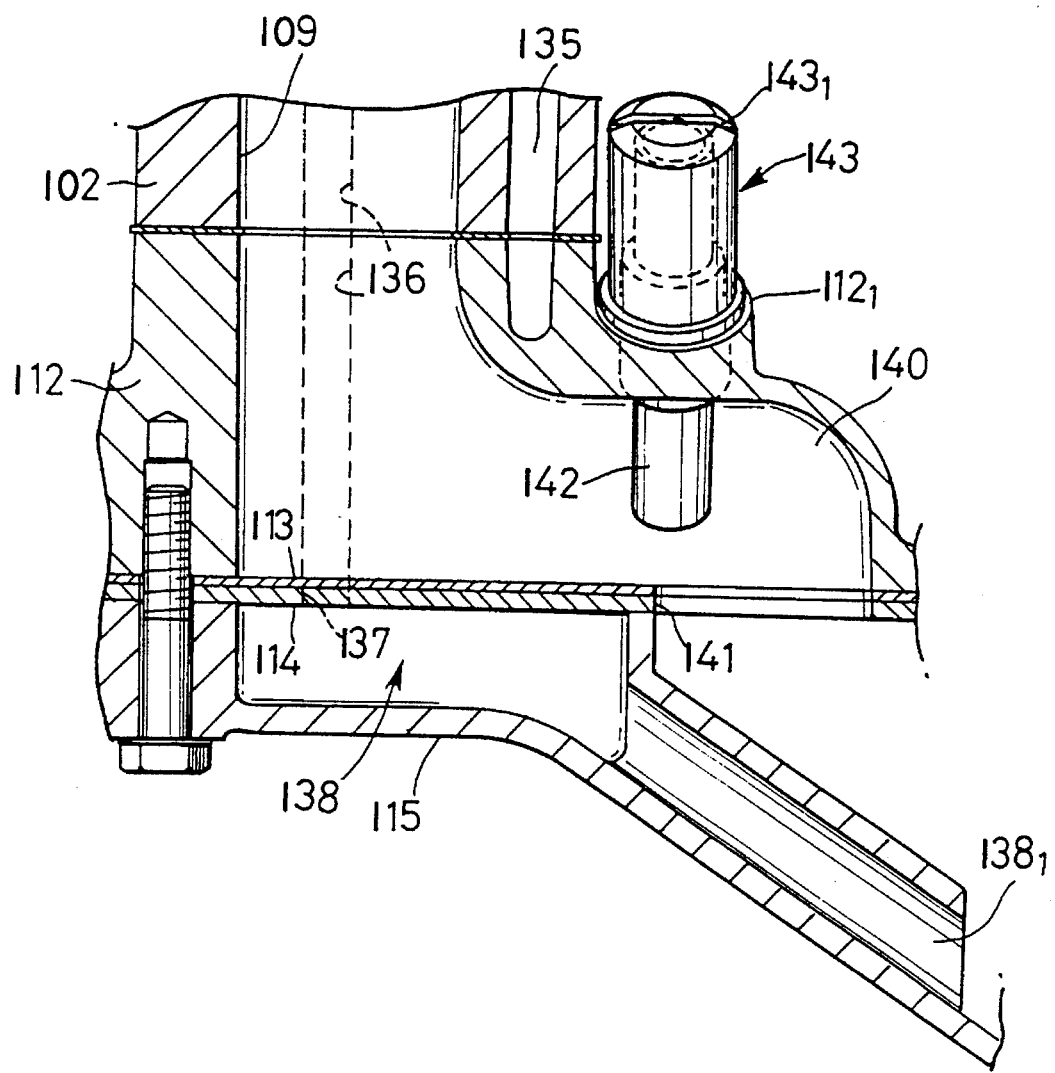
Figure 24:
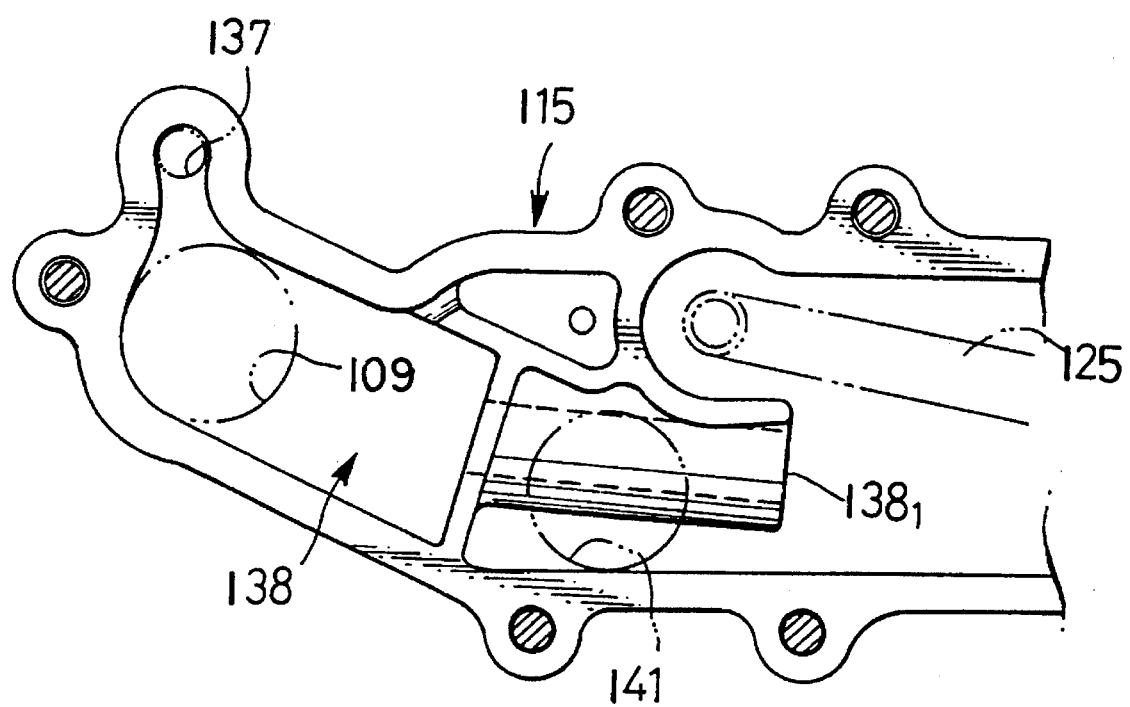

A flat seat surface $112_1$ FIG. 22 inclined obliquely upwardly and leftwardly is formed on an outer wall of the exhaust block 112. An exhaust gas sampling pipe 142 formed at including a straight stud pipe, is threadedly inserted from the seat surface $112_1$ into a thick-formed wall of the exhaust block 112. The exhaust gas sampling pipe 142, is passed through the exhaust block 112, and is opened into the exhaust passage 140. A plug 143, having a minus groove $143_1$ engageable by a tip end of a driver, is threadedly fitted over the exhaust gas sampling pipe 142, and the sealing member 144 is clamped between the plug 43 and the seat surface $112_1$ of the exhaust block 112, thereby occluding the opened end of the exhaust gas sampling pipe 142 to prevent a leakage of an exhaust gas.

In measuring the components of the exhaust gas, the engine cover 116 is separated from the undercase 157, and the plug 43 is removed from the exhaust gas sampling pipe 142. A tube connected to a component measuring instrument (not shown) is connected to the pipe 42 and pulled outside from the air inlet $157_1$ or the $157_2$, and the engine cover 116 is closed, thereby enabling the sampling of the exhaust gas through the exhaust passage 140.

The exhaust gas sampling pipe 142 is supported in the exhaust block 112 and located therewithin, so that the plug 143 occluding the tip end of the exhaust gas sampling pipe 142 is not passed through the engine cover 116 and the undercase 157. Therefore, of an opening for permitting the exhaust gas sampling pipe 142 to be led outside need not be provided in the engine cover 16 or the undercase 157, leading to an improved sealability, but also by covering the plug 143 occluding the opened end of the exhaust gas sampling pipe 142 with the engine cover 116 and the undercase 115, it is possible to prevent the minus groove $143_1$ from being filled up or shallowed due to precipitated salt, rust or corrosion resulting from deposition of seawater, thereby influencing the workability. Moreover, it is possible to avoid the generation of a rust or corrosion due to the deposition of seawater on the exhaust block 112 to which the exhaust gas sampling pipe 142 is attached, and to prevent a degradation of appearance. Further, it is possible to prevent the exhaust gas sampling pipe 142 from being brought into contact with another object and damaged during transportation of the outboard motor When the tube connected to the component measuring instrument is connected, the horizontal projecting of the exhaust gas sampling pipe 142 can be suppressed, because the exhaust gas sampling pipe 142 extends obliquely upwardly, thereby insuring a sufficient space between the pipe 42 itself and the peripheral edge of the opening at the upper end of the undercase 157 to facilitate the mounting of the tube. During this time, it is possible to prevent the interference between the tube and the components of the outboard motor O to further facilitate the mounting of the tube, because the exhaust gas sampling pipe 142 is inclined toward the outside of the outboard motor O.

Figure 25:
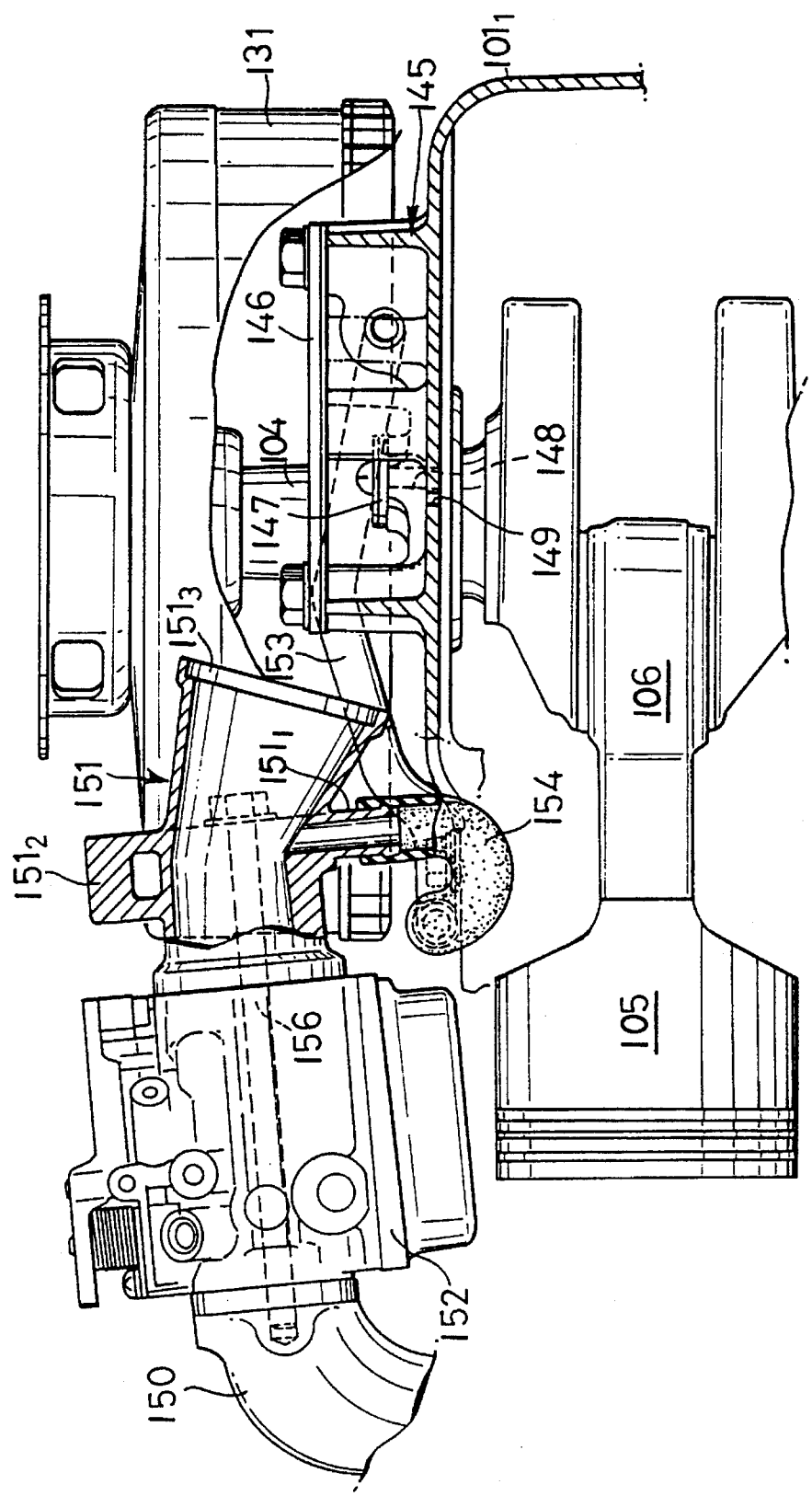

As can be seen from FIGS. 21 and 25, an oil separating chamber 145 is integrally defined in an upper wall of the crank case section $1_1$ of the engine block 1. A top surface of the oil separating chamber 45 is closed by a detachable lid 146, and an internal space in the oil separating chamber 145 and the interior of the crank case portion $101_1$ communicate with each other through a blow-by gas passage 148 closed by a one-way valve 147 and through an oil return hole 149. The interior oil separating chamber 145 is partitioned in a labyrinth-like configuration, and an oil and mist contained in a blow-by gas flowing from the inside of the crank case portion $101_1$ through the one-way valve 147 into the oil separating chamber 145 are separated. Then, the separated oil is returned by gravity through the oil return hole 149 defined in a bottom surface of the oil separating chamber 145 into the crank case portion $101_1$. The oil return hole 149 is occluded by steel wool.

An air intake 151 and a carburettor 152 are provided upstream of an intake pipe 150 connected to the cylinder head 102. The air intake 151 is a substantially cylindrical member including a mounting flange $151_2$ at an end thereof adjacent the carburettor 152 and a downwardly inclined opening $151_3$ at the other end thereof. The air intake 151 and the carburetor 152 are co-fastened to the intake pipe 151 by two bolts 156, 156 passed through left and right sides of the mounting flange $151_2$. The air intake 151 is a member of synthetic resin and is injection-molded by a vertically split metal mold. In this molding, a downwardly extending connector $151_1$ is integrally formed on a lower surface of the air intake 151.

A blow-by gas passage 153 comprises a metal pipe connected at its base end to a sidewall of the oil separating chamber 145 extends toward the air intake 151. A tip end of the passage 153 is connected to the connector $151_1$ of the air intake 151 through a blow-by gas passage 154 defined by a U-curved rubber joint. Thus, the mist resulting from separation of the oil in the oil separating chamber 145 is sucked by a suction negative pressure and drawn through the air intake 151 into the carburetor 152.

The air intake 151 is fixed to the carburetor 152 by two bolts 156, 156 passed through the left and right sides of the mounting flange $151_2$, but the connector $151_1$ connecting the blow-by gas passage 154 to the air intake 151 is provided on a lower surface of the air intake 151, and moreover, the blow-by gas passage 154 connected to the connector $151_1$ extends toward the oil separating chamber 145 in a U-curved configuration. Therefore, in attaching or detaching the air intake 151 by operation of the bolts 156, 156, the blow-by gas passage 154 cannot interfere with a tool to obstruct the working. In addition, because the connector $151_1$ is provided on the lower surface of the air intake located at a higher position, it is possible to shorten the length of each of the blow-by gas passages 153 and 154 extending from the connector $151_1$ to the oil separating chamber 145 located at a lower position.

As is apparent from FIG. 25, the blow-by gas passage 153 extends obliquely upwardly from the oil separating chamber 145 by utilizing an internal space in the flywheel 131 and then obliquely downwardly from its top point and is connected to the air intake 151. In this manner, a portion of the blow-by gas passage 153 near a connection thereof with the oil separating chamber 145 is inclined downwardly, thereby ensuring that a portion of the oil deposited and captured within the blow-by gas passage 153 is returned into the oil separating chamber 145 and is difficult to be resident therein. Therefore, it is possible to prevent the oil from being drawn into the intake system at one time.

As can be seen from FIG. 21, the outboard motor O removed from a hull is placed laterally, so that supporting projections 155, 155 come into contact with a ground surface GL, and at this time, the carburetor 152 is located below the cylinder head 102. The blow-by gas passage 153 interconnecting the oil separating chamber 145 and the air intake 151 is disposed in an inverted U-shaped configuration so as to pass above the crank shaft 104. This prevents the oil accumulated in the oil separating chamber 145 from flowing therefrom into the intake system, when the outboard motor O is placed in a horizontal attitude.

A fifth embodiment of the present invention will now be described with reference to FIGS. 26 to 31.

Figure 26:
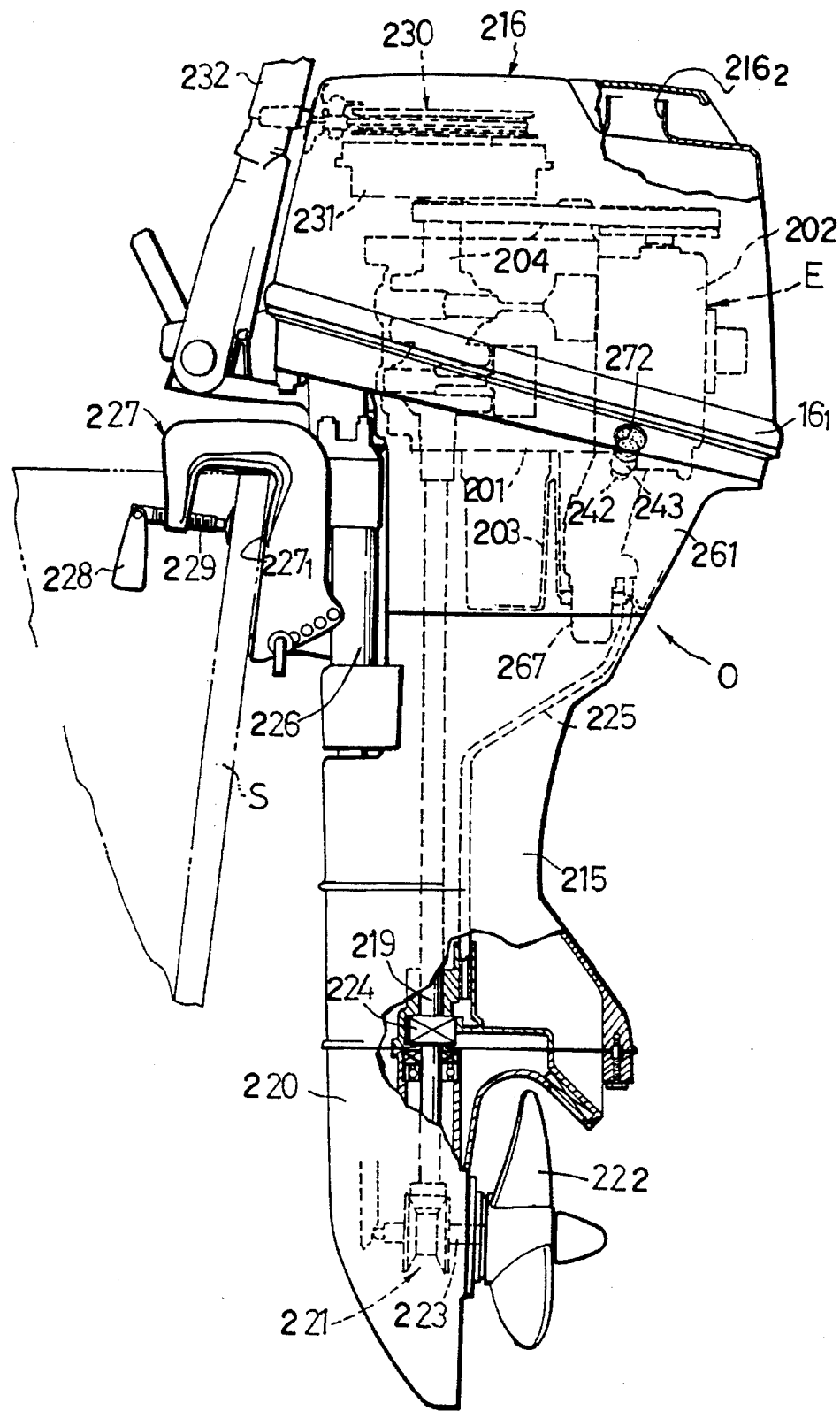

As shown in FIG. 26, an outboard motor O of the fifth embodiment includes an oil case 261 interposed between the extension case 215 and the engine block 201. An oil pan 203 is integrally formed within the oil case 261, and an engine cover 215 is detachably coupled to an opening at an upper end of the oil case 261.

Figure 27:
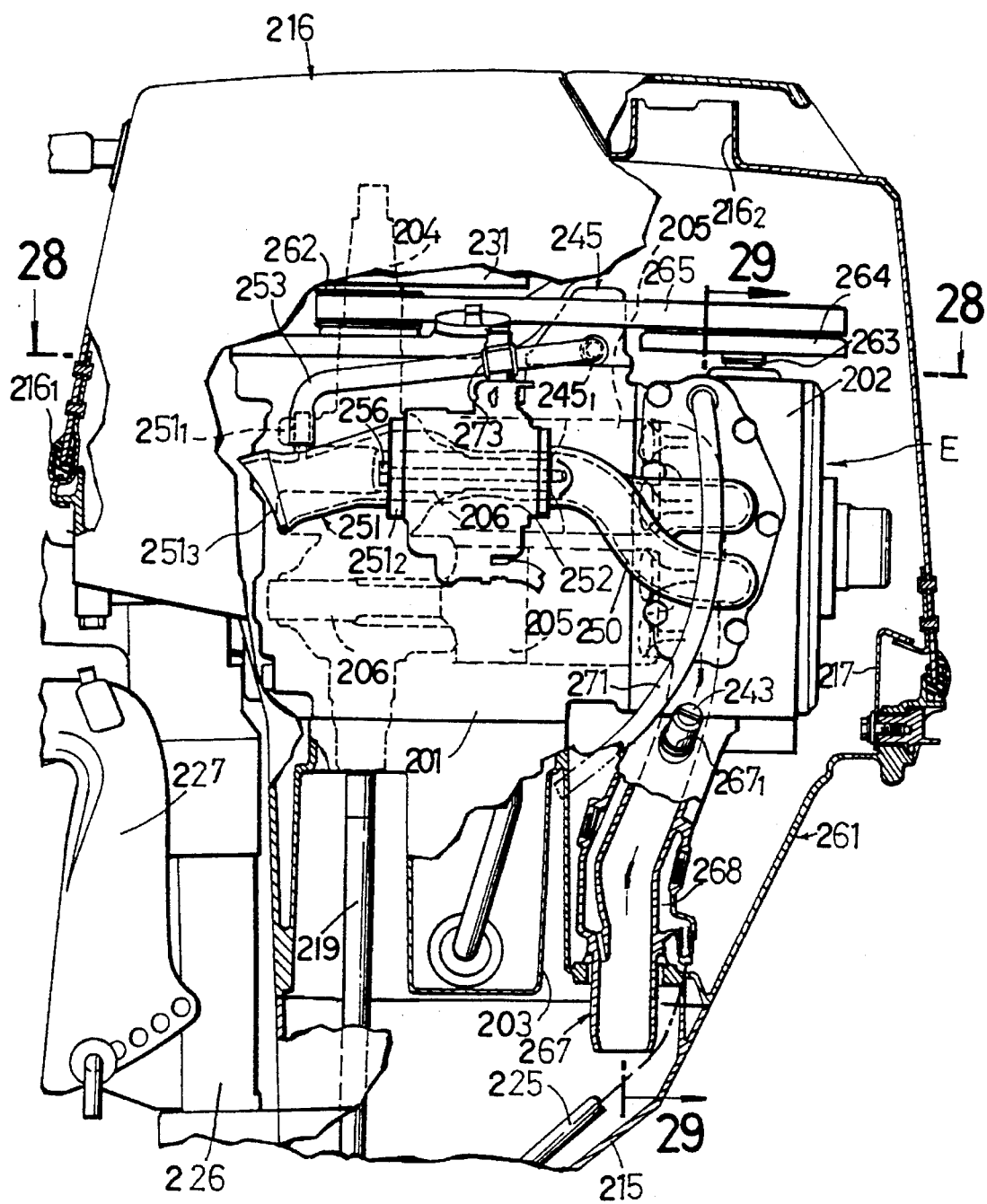
Figure 28:
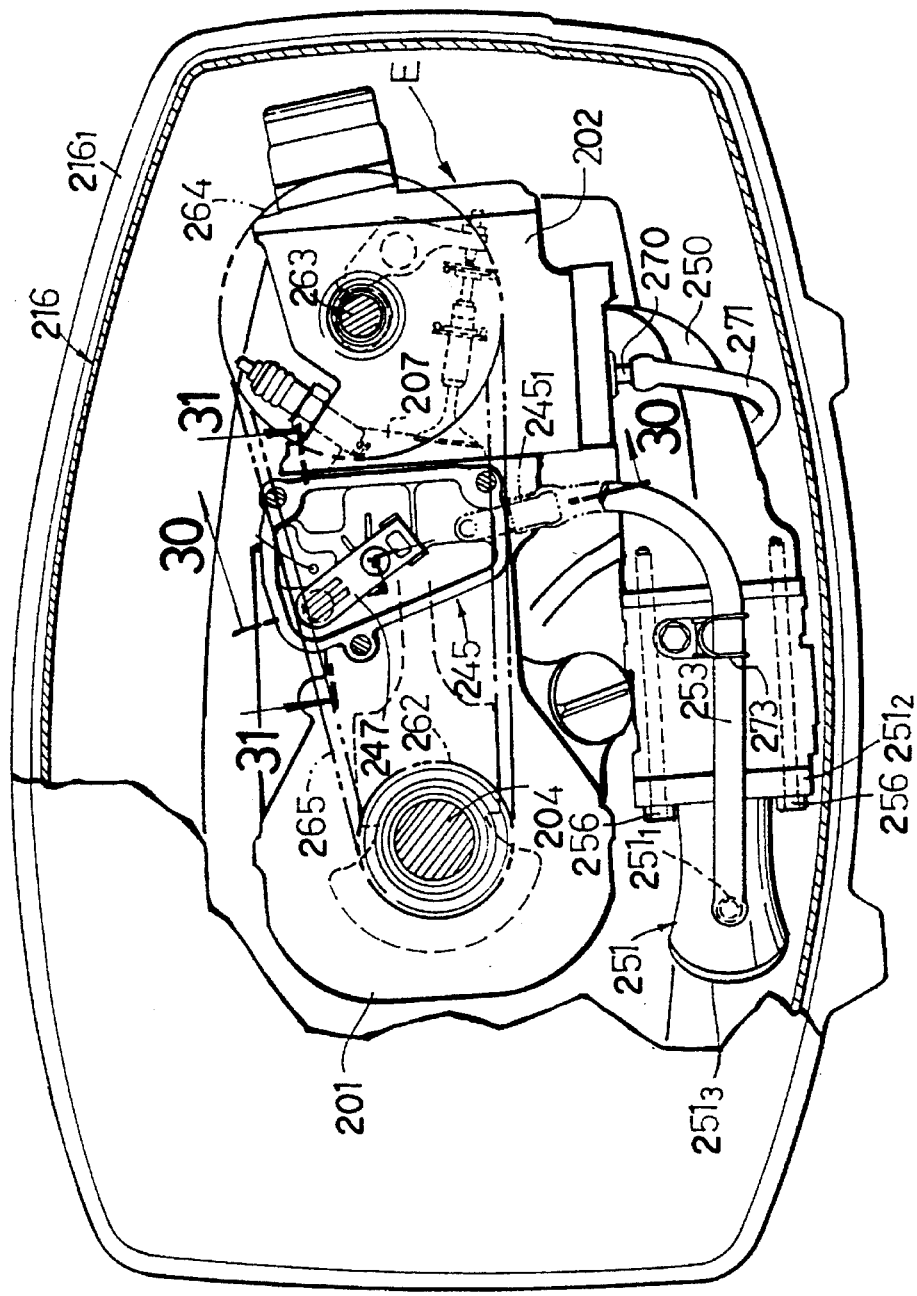

As shown in FIGS. 27 and 28, a 2-cylinder type vertical engine E, accommodated in the engine cover 215 includes a engine block 201 supported at an upper end of lower oil case 261, and a cylinder head 202 coupled to the engine block 201. A timing belt 265 is wound around a driving pulley 263 mounted on a crank shaft 204 projecting upwardly from the engine block 201 and around a follower pulley 264 mounted on a cam shaft 263 projecting upwardly from the cylinder head 202. A carburetor 252 and an air intake 251 are connected to a front end of an intake pipe 250 extending from a left side of the cylinder head 202 toward the front of the outboard motor O.

Figure 29:
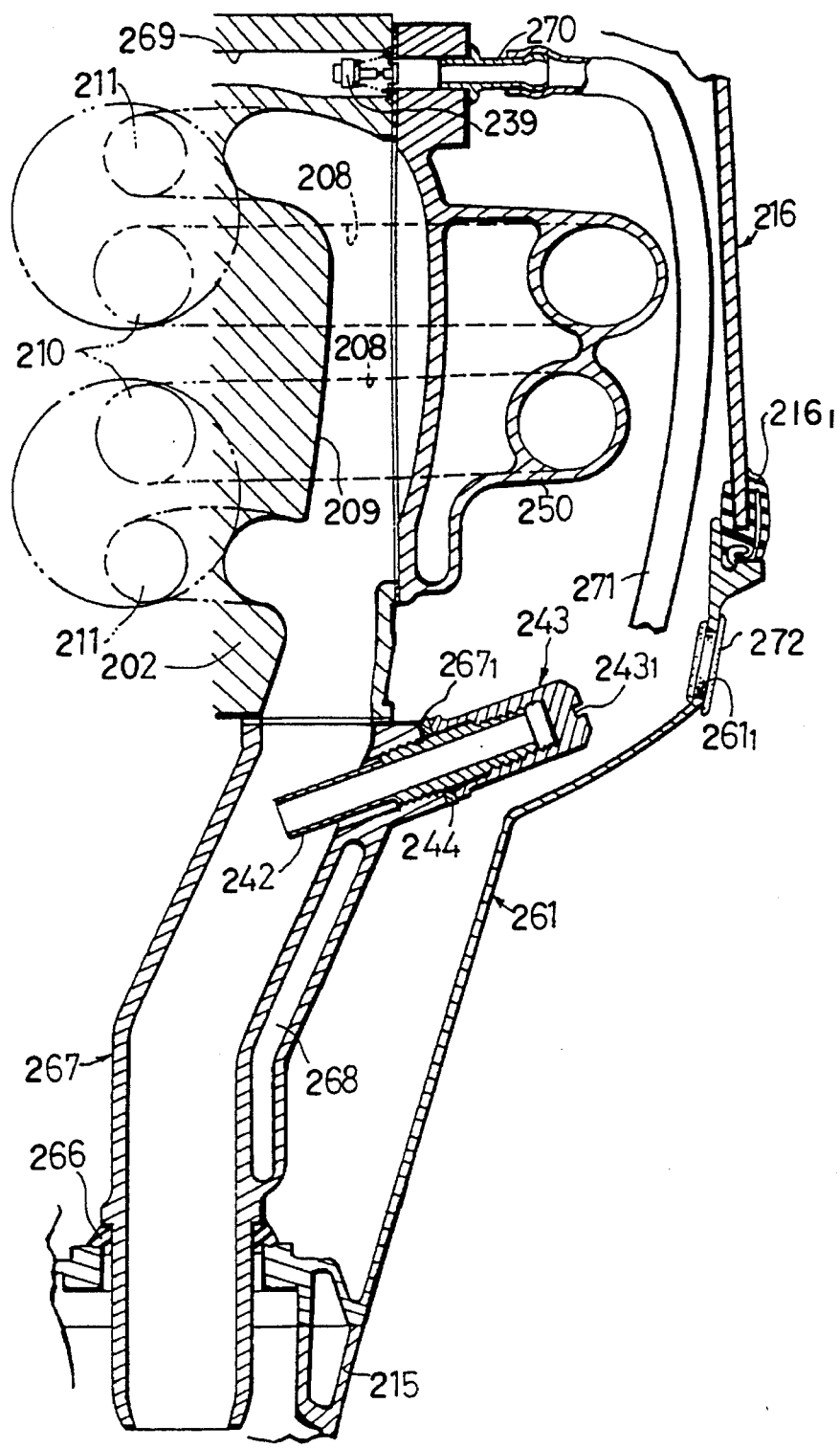
Figure 30:
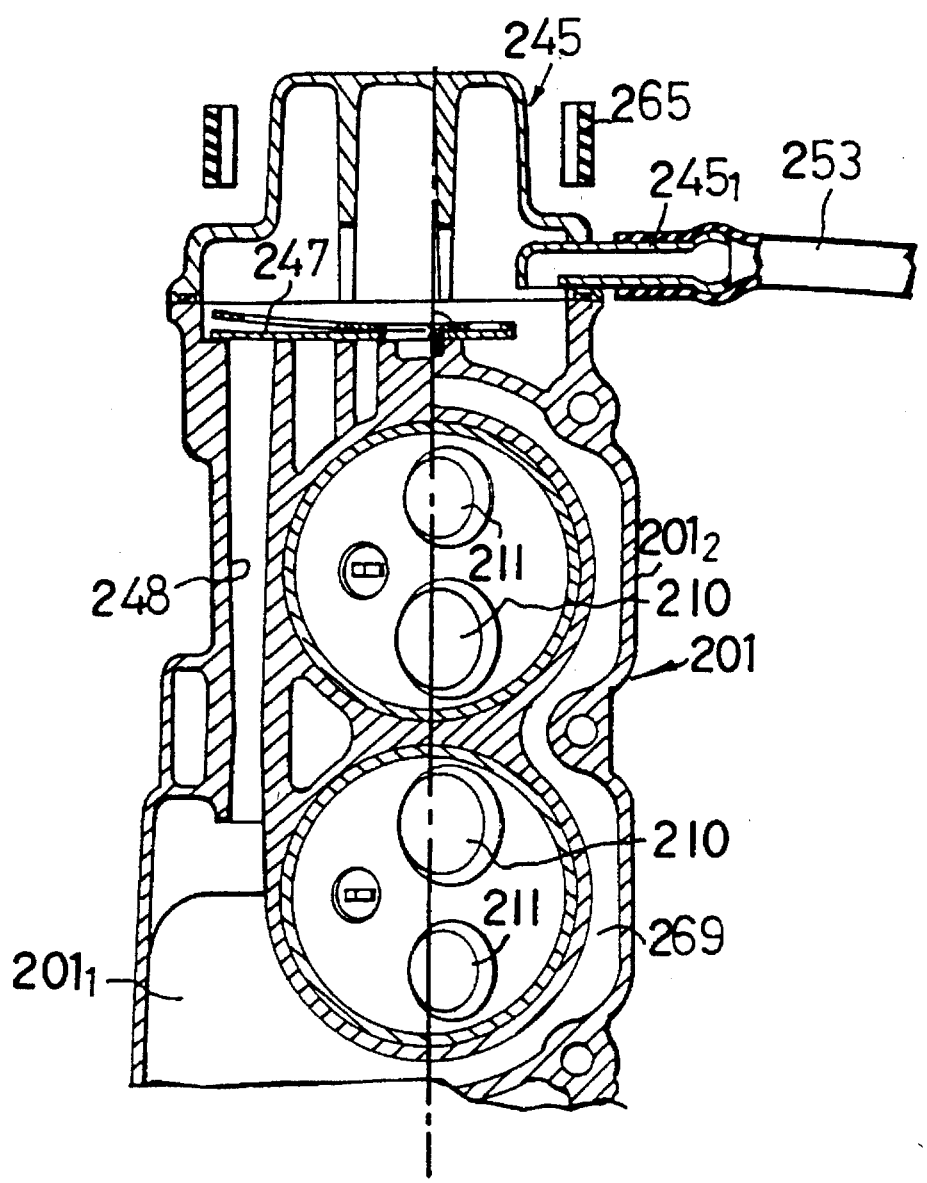
Figure 31:
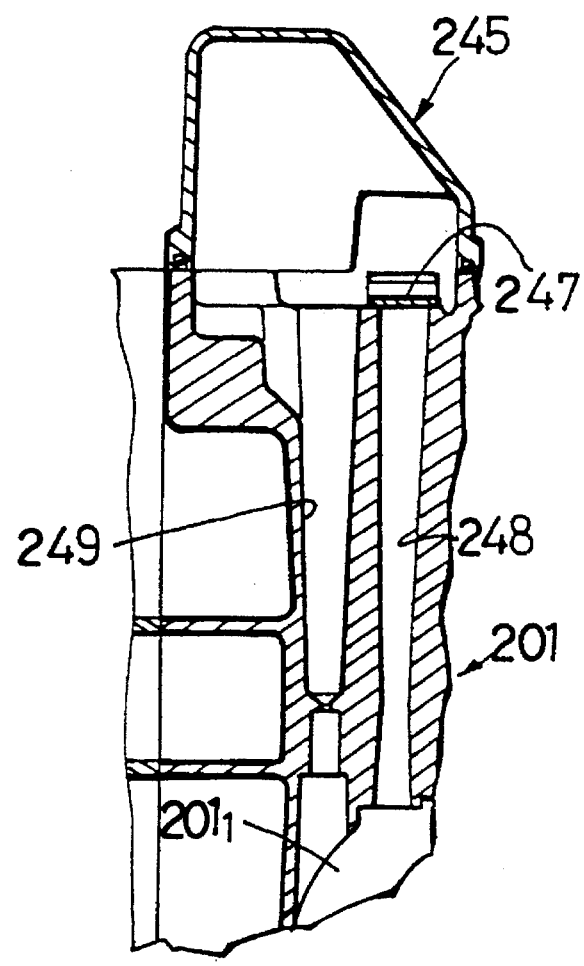

As can be seen from FIGS. 27, 29 and 30, an exhaust pipe 267 passed through the lower case 261 with a sealing member 266 interposed therebetween is coupled to a lower surface of the cylinder head 202 and is opened at its lower end into the extension case 15. A cooling water pipe 225, FIG. 27, extending upwardly from a cooling water pump 224 (see FIG. 26) is connected to a lower end of a water jacket 268 defined around an outer periphery of the exhaust pipe 267. The water jacket 268 has an upper end connected to a lower end of a water jacket 269 (see FIG. 30) defined in the cylinder head 202 and the cylinder block portion $201_2$ of the engine block 201. An upper end of the water jacket 269 in the cylinder head 2 is connected to a drainage pipe 271 through a thermostat 239 and a connector 270 (see FIG. 29) mounted on an outer wall of the intake pipe 250. The drainage pipe 271 extends downwardly and is opened into an internal space in the extension case 215.

A flat seat surface $267_1$ inclined obliquely upwardly and leftwardly, is formed on a thicker portion of the exhaust pipe 267 in the vicinity of its upper end. An exhaust gas sampling pipe 242 is threadedly inserted into the seat surface $267_1$ and has either the same structure as the exhaust gas sampling pipe 242 in the fourth embodiment or a structure in which a cylindrical threaded portion is integrally formed around an outer periphery of a straight pipe by welding or the like. A plug 243 threadedly filled over a tip end of the exhaust gas sampling pipe 242 is accommodated in an internal space in the oil case 261, and an opening $261_1$ is defined in the oil case 261, so that a tip end of a driver is brought into engagement in a minus groove $143_1$ in the plug 243 to remove the plug 243 from the exhaust gas sampling pipe 242. The opening $261_1$ in case 261 is closed by a detachable cap 272 of a rubber to prevent the ingress of water.

In measuring components in an exhaust gas, the engine cover 216 may be separated from the oil case 261, following which the plug 243 loosened by insertion of a driver through the opening $261_1$ with the cap 272 removed therefrom may be removed from the opening in the upper surface of the oil case 261, which is provided by removal of the engine cover 216, and a tube of a component measuring instrument inserted through the air inlet $216_2$ (see FIG. 27) in the engine cover 216 may be connected to the opened end of the exhaust gas sampling pipe 242. It should be noted that the opening $261_1$ in the oil case 261 may be of a larger diameter, so that the plug 243 and/or the tube can be removed, there through However, if the opening $2161_1$ is of a smaller diameter, the provision of a smaller cap 272 suffices.

Even with the fifth embodiment, it is possible to cover the plug 243 occluding the tip end of the exhaust gas sampling pipe 242 with the engine cover 16 and the oil case 261 to protect the plug 204 against a rust due to the deposition of seawater. Moreover, it is possible to prevent the exhaust gas sampling pipe 242 from being brought into contact with another object and damaged during transportation of the outboard motor O. The horizontal projecting of the exhaust gas sampling pipe 242 can be suppressed by oblique upward inclination of the exhaust gas sampling pipe 242, thereby insuring a space used for the mounting of the tube between the pipe 242 and he peripheral edge of the opening at the upper end of the oil case 261 to facilitate the mounting of the tube. Moreover, it is possible to prevent the interference between the tube and the components of the outboard motor O by the inclination of the exhaust gas sampling pipe 242 toward the outside of the outboard motor O.

As can be seen from FIGS. 27, 28, 30 and 31, an oil separating chamber 245 is provided at an upper surface of the engine block 201 to lie between a tensioned side and loosened side of the timing belt 265. The inside of the oil separating chamber 245 communicates with the inside of the crankcase portion $201_1$ through the blow-by gas passage 248 extending vertically through a sidewall of the crankcase portion $201_1$. A one-way valve 247 for opening and closing the blow-by gas passage 248 is mounted in a bottom wall of the oil separating chamber 245, and the inside of the oil separating chamber 245 communicates with the inside of the crankcase portion $201_1$ through the oil return hole 249.

An air intake 251 and a carburetor 252 are co-fastened to the intake pipe 250 connected to the cylinder head 202 by two bolts 156, 156. The air intake 251 of a synthetic resin is injection-molded by a vertically split metal mold as in the fourth embodiment and includes a mounting flange $251_2$ and an opening $251_3$ at opposite ends thereof, but a connector $251_1$ is integrally formed in an upwardly directed manner on an upper surface of the air intake 251, unlike the fourth embodiment.

The blow-by gas passage 53 made of a flexible pipe connecting the connector $45_1$ provided on the oil separating chamber 245 with the connector $251_1$ provided on the air intake 251 extends from the oil separating chamber 245 and is declined monotonously from a location beyond the upper surface of the engine E toward the air intake 251, with its intermediate portion fixed to an upper surface of the carburetor 252 by a clip 273 (see FIG. 27). Because the blow-by gas passage 253 has no loosened portion in this manner, an oil deposited on a wall surface of the blow-by gas passage 253 flows promptly into the air intake 251 without residence. A small amount of oil flowing into the blow-by gas passage 253 is discharged into the air intake at every time and thus, the sudden flowing of a large amount of oil into the intake system is prevented.

Because the two left and right bolts 256, 256 for fixing the air intake 251 to the carburetor 252 lie at locations spaced apart from the blow-by gas passage 253 extending upwardly from the connector 251₁ provided on the air intake 251, it is possible to easily conduct the attaching and detaching of the air intake 251 by operation of the bolts 256, 256. In addition, since the connector 251₁ is provided on the upper surface of the air intake 251 lying at a lower position, it is possible to shorten the length of the blow-by gas passage 253 extending from the connector 251₁ to the oil separating chamber 245 lying at a higher position.

What is claimed is:

1. An exhaust gas sampling device/or an outboard motor comprising an engine, a propeller driven by said engine, case means for rotatably supporting said propeller, cover means detachably mounted on said case means, an exhaust passage for introducing an exhaust gas from said engine to a lower portion of said case means, and an exhaust gas sampling pipe having opposite opened ends and connected at one of said opposite ends to said exhaust passage, wherein the other of said opposite opened ends of said exhaust gas sampling pipe is disposed within a space which is defined inside said case means and said cover means and which is separated from said exhaust passage, said other opened end of the exhaust gas sampling means being normally closed by a plug means removable while said exhaust gas is being sampled.

2. An exhaust gas sampling device for an outboard motor according to claim 1, wherein said exhaust passage is an exhaust pipe extending from the engine.

3. An exhaust gas sampling device for an outboard motor according to claim 2, wherein an outer periphery of said exhaust pipe is covered with a two-divided exhaust pipe cover to form a cooling-water passage, and said exhaust gas sampling pipe is clamped between matching surfaces of said exhaust pipe cover.

4. An exhaust gas sampling device for an outboard motor according to claim 1, wherein said exhaust passage is formed in a mounting member clamped between the engine and an extension case.

5. An exhaust gas sampling device for an outboard motor according to claim 4, wherein said mounting member is formed with an oil passage substantially in parallel to said exhaust passage, said oil passage being connected to an oil pan, and the exhaust gas sampling pipe mounted in said exhaust passage is disposed at a position which does not interfere with said oil passage.

6. An exhaust gas sampling device for an outboard motor according to claim 1, wherein said cover means is an engine cover covering the engine.

7. An exhaust gas sampling device for an outboard motor according to claim 1, wherein said seat surface of said exhaust gas passage is inclined toward the outside of the outboard motor.

8. An exhaust gas sampling device for an outboard motor according to claim 1, further comprising means for mounting said engine to said cover means, said exhaust passage being defined in said means for mounting said engine to said cover means, said space being defined between said means for mounting said engine to said cover means and one of said case means and said cover means.

9. An exhaust gas sampling device for an outboard motor according to claim 8, wherein an opening is provided in one of said case means and said cover means for providing an access to said exhaust gas sampling pipe from an outside of said outboard motor.

10. An exhaust gas sampling device for an outboard motor according to claim 1, wherein an opening is provided in one of said case means and said cover means for providing an access to said exhaust gas sampling pipe from an outside of said outboard motor.

11. An exhaust gas sampling device for an outboard motor comprising an engine, a propeller driven by said engine, case means for rotatably supporting said propeller, cover means detachably mounted on said case means, an exhaust passage for introducing an exhaust gas from said engine to a lower portion of said case means, and an exhaust gas sampling pipe having opposite opened ends and connected at one of said opposite ends to said exhaust passage, wherein the other of said opposite opened ends of said exhaust gas sampling pipe is disposed within a space which is defined inside said case means and said cover means and which is separated from said exhaust passage, said other opened end of the exhaust gas sampling means being normally closed by a removable plug means, wherein said cover means is an undercover connected to a lower portion of an undercase covering the engine.

12. An exhaust gas sampling device for an outboard motor, according to claim 11, wherein said undercover is provided with a circular opening at a location to which said exhaust gas sampling pipe faces.

13. An exhaust gas sampling device for an outboard motor according to claim 12, wherein said circular opening is normally closed by a removable cap.

14. An exhaust gas sampling device for an outboard motor according to claim 11, wherein said undercover is provided with a U-shaped opening at a location to which said exhaust gas sampling pipe faces.

15. An exhaust gas sampling device for an outboard motor according to claim 14, wherein said U-shaped opening is normally closed by a removable cap.

16. An exhaust gas sampling device for an outboard motor comprising an engine, a propeller driven by said engine, case means for rotatably supporting said propeller, an exhaust gas outlet passage which connects an exhaust bore in said engine with an exhaust chamber provided in said case means to introduce an exhaust gas from the engine to a lower portion of said case means, and an exhaust gas sampling pipe which is mounted in an outer wall member defining said exhaust gas outlet passage therein and which is connected at one of opposite opened ends thereof to said exhaust gas outlet passage, wherein said exhaust gas sampling pipe is a stud pipe embedded into said outer wall member, and said outer wall member is formed with a sealing surface against which a removable plug for normally closing the other of said opposite opened ends of said exhaust sampling pipe abuts, said other opened end of the exhaust gas sampling pipe and said removable plug being disposed in a space which is defined inside at least one of said case means and said cover means which is separated from said exhaust gas outlet passage.

17. An exhaust gas sampling device for an outboard motor according to claim 16, wherein cover means is provided for covering said engine and an opening is provided in one of said case means and said cover means for providing an access to said exhaust gas sampling pipe from an outside of said outboard motor.

18. An exhaust gas sampling device for an outboard motor comprising an engine, a propeller driven by said engine, case means for rotatably supporting said propeller, an exhaust gas outlet passage which connects an exhaust bore in said engine with an exhaust chamber provided in said case means to introduce an exhaust gas from the engine to a lower portion of said case means, and an exhaust gas sampling pipe which is mounted in an outer wall member defining said exhaust gas outlet passage therein and which is connected at one of opposite opened ends thereof to said exhaust gas outlet passage, wherein said exhaust gas sampling pipe is a stud pipe embedded into said outer wall member, and said outer wall member is formed with a sealing surface against which a removable plug for normally closing the other of said opposite opened ends of said exhaust sampling pipe abuts, said other opened end of the exhaust gas sampling pipe and said removable plug being disposed in a space which is defined inside said case means and which is separated from said exhaust gas outlet passage, wherein said exhaust gas sampling pipe is formed with an abutment for receiving a jig for threadedly fitting said exhaust gas sampling pipe into said outer wall member.

19. An exhaust gas sampling device for an outboard motor comprising an engine, a propeller driven by said engine, case means for rotatably supporting said propeller, cover means detachably mounted to said case means and forming with said case means an internal space, an exhaust passage through which an exhaust gas is passed from said engine to a lower portion of said case means, and an exhaust gas sampling pipe connected at one of opposite opened ends thereof to the exhaust gas passage, wherein said exhaust gas sampling pipe is formed substantially straight and is mounted from above to a seat surface formed in an upwardly-directed manner on an outer surface of a thick wall defining said exhaust gas passage, and said exhaust gas sampling device further include a removable plug located in an internal passage defined in said cover means and/or said case means for normally closing the other of said opposite opened ends of said exhaust gas sampling pipe, said internal space being separated from said exhaust gas passage.

20. An exhaust gas sampling device for an outboard motor according to claim 19, wherein an opening is provided in one of said case means and said cover means for providing an access to said exhaust gas sampling pipe from an outside of said outboard motor.

21. An exhaust gas sampling device for an outboard motor comprising an engine, a propeller driven by said engine, case means for rotatably supporting said propeller, cover means detachably mounted on said cover case means, an exhaust passage for introducing an exhaust gas from said engine to a lower portion of said case means, and an exhaust gas sampling pipe connected to said exhaust passage, wherein an opened end of said exhaust gas sampling pipe is located within a space which is defined by said case means and said cover means and said cover means is an undercover connected to a lower portion of an undercase covering the engine.

22. An exhaust gas sampling device for an outboard motor according to claim 21, wherein said undercover is provided with a circular opening at a location to which said exhaust gas sampling pipe faces.

23. An exhaust gas sampling device for an outboard motor according to claim 21, wherein said undercover is provided with a U-shaped opening at a location to which said exhaust gas sampling pipe faces.

24. An exhaust gas sampling device for an outboard motor comprising an engine, a propeller driven by said engine, case means for rotatably supporting said propeller, cover means detachably mounted on said case means, an exhaust passage for introducing an exhaust gas from said engine to a lower portion of said case means, and an exhaust gas sampling pipe connected to said exhaust passage, wherein an opened end of said exhaust gas sampling pipe for receiving said exhaust gas from said exhaust passage is disposed in said exhaust passage and an opposite closable end of said exhaust sampling pipe is disposed in a space between said exhaust passage and said cover means.

* * * * *